US010435404B2

(12) United States Patent
Ibrahim et al.

(10) Patent No.: US 10,435,404 B2
(45) Date of Patent: Oct. 8, 2019

(54) FORMULATIONS OF A COMPOUND MODULATING KINASES

(71) Applicants: Plexxikon Inc., Berkeley, CA (US); Daiichi Sankyo Company, Limited, Tokyo (JP)

(72) Inventors: Prabha N. Ibrahim, Mountain View, CA (US); Hamid Rezaei, Berkeley, CA (US); Gary Conard Visor, Castro Valley, CA (US); Tomoari Kamo, Tokyo (JP); Hiroshi Yamakose, Tokyo (JP)

(73) Assignees: Plexxikon Inc., Berkeley, CA (US); Daiichi Sankyo Company, Limited, Tokyo (JP)

(*) Notice: Subject to any disclaimer, the term of this patent is extended or adjusted under 35 U.S.C. 154(b) by 0 days.

(21) Appl. No.: 16/043,821

(22) Filed: Jul. 24, 2018

(65) Prior Publication Data

US 2019/0031654 A1 Jan. 31, 2019

Related U.S. Application Data

(60) Provisional application No. 62/536,574, filed on Jul. 25, 2017.

(51) Int. Cl.

| | |
|---|---|
| *C07D 471/04* | (2006.01) |
| *A61K 45/06* | (2006.01) |
| *A61K 9/48* | (2006.01) |
| *A61K 31/444* | (2006.01) |
| *A61P 25/00* | (2006.01) |
| *A61P 27/00* | (2006.01) |
| *A61P 9/00* | (2006.01) |
| *A61P 25/28* | (2006.01) |
| *A61P 35/04* | (2006.01) |
| *A61P 35/00* | (2006.01) |
| *A61P 35/02* | (2006.01) |
| *A61P 19/10* | (2006.01) |
| *A61P 25/18* | (2006.01) |
| *A61P 31/18* | (2006.01) |
| *A61P 43/00* | (2006.01) |
| *A61P 25/08* | (2006.01) |
| *A61K 47/10* | (2017.01) |
| *A61K 47/12* | (2006.01) |
| *A61K 47/22* | (2006.01) |
| *A61K 47/26* | (2006.01) |

(52) U.S. Cl.
CPC .......... *C07D 471/04* (2013.01); *A61K 9/4825* (2013.01); *A61K 9/4858* (2013.01); *A61K 9/4866* (2013.01); *A61K 31/444* (2013.01); *A61K 45/06* (2013.01); *A61K 47/10* (2013.01); *A61K 47/12* (2013.01); *A61K 47/22* (2013.01); *A61K 47/26* (2013.01); *A61P 9/00* (2018.01); *A61P 19/10* (2018.01); *A61P 25/00* (2018.01); *A61P 25/08* (2018.01); *A61P 25/18* (2018.01); *A61P 25/28* (2018.01); *A61P 27/00* (2018.01); *A61P 31/18* (2018.01); *A61P 35/00* (2018.01); *A61P 35/02* (2018.01); *A61P 35/04* (2018.01); *A61P 43/00* (2018.01); *C07B 2200/13* (2013.01)

(58) Field of Classification Search
CPC .................................................... C07D 471/04
USPC ........................................................ 514/300
See application file for complete search history.

(56) References Cited

U.S. PATENT DOCUMENTS

| | | | |
|---|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |

(Continued)

FOREIGN PATENT DOCUMENTS

| | | |
|---|---|---|
| WO | WO 2007/013896 | 2/2007 |
| WO | WO 2008/063888 | 5/2008 |

(Continued)

OTHER PUBLICATIONS

Bodratti, J. Funct. Biomater. Sep. 11, 2018.*
U.S. Appl. No. 16/158,107, filed Oct. 11, 2018, Ibrahim et al.
U.S. Appl. No. 16/172,573, filed Oct. 26, 2018, Rezaei et al.
U.S. Appl. No. 16/219,730, filed Dec. 13, 2018, Ibrahim et al.

(Continued)

*Primary Examiner* — Nizal S Chandrakumar
(74) *Attorney, Agent, or Firm* — Sheppard Mullin Richter & Hampton LLP

(57) ABSTRACT

Provided are compositions comprising Compound I having the following structure:

Compound I

[chemical structure]

or a pharmaceutically acceptable salt thereof, and a solubilizing agent; methods of making the same; and methods of using the same.

20 Claims, 8 Drawing Sheets

(56) References Cited

U.S. PATENT DOCUMENTS

| | | |
|---|---|---|
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Diodone et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim et al. |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0038948 A1 | 2/2014 | Wu et al. |
| 2014/0128390 A1 | 5/2014 | Lin et al. |
| 2014/0303121 A1 | 10/2014 | Zhang et al. |
| 2014/0303187 A1 | 10/2014 | Wu et al. |
| 2015/0290205 A1 | 10/2015 | Ibrahim et al. |
| 2016/0176865 A1 | 6/2016 | Ibrahim et al. |
| 2016/0326162 A1 | 11/2016 | Lin et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0158690 A1 | 6/2017 | Wu et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |
| 2018/0002332 A1 | 1/2018 | Ibrahim et al. |
| 2018/0030051 A1 | 2/2018 | Ibrahim et al. |
| 2018/0055828 A1 | 3/2018 | Bollag |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim |
| 2018/0111930 A1 | 4/2018 | Desai |
| 2018/0215763 A1 | 8/2018 | Wu et al. |
| 2018/0265508 A1 | 9/2018 | Lin |

FOREIGN PATENT DOCUMENTS

| | | | | |
|---|---|---|---|---|
| WO | WO 2008063888 | * | 5/2008 | ........... C07D 47/104 |
| WO | WO 2010/111527 | | 9/2010 | |
| WO | WO 2010/129467 | | 11/2010 | |
| WO | WO 2016/179415 | | 11/2016 | |
| WO | WO 2016/188816 | | 12/2016 | |

OTHER PUBLICATIONS

Daiichi Sankyo. Investigator's Brochure Pexidartinib (PLX3397). England ISBN: 978-0-08-026201-7. Oct. 26, 2016. pp. 1-165.

International Search Report and Written Opinion dated Oct. 25, 2018 for PCT/US2018/043433. 16 pages.

Mok, et al. Inhibition of CSF-1 receptor improves the antitumor efficacy of adoptive cell transfer immunotherapy. Cancer Res. Jan. 1, 2014;74(1):153-161. doi: 10.1158/0008-5472.CAN-13-1816. Epub Nov. 18, 2013.

Tap, et al. Structure-Guided Blockade of CSF1R Kinase in Tenosynovial Giant-Cell Tumor. N Engl J Med. Jul. 30, 2015;373(5):428-37. doi: 10.1056/NEJMoa1411366.

U.S. Appl. No. 15/977,772, filed May 11, 2018, Ibrahim et al.
U.S. Appl. No. 16/001,534, filed Jun. 6, 2018, Zhang et al.
U.S. Appl. No. 16/024,197, filed Jun. 29, 2018, Ibrahim et al.
U.S. Appl. No. 16/058,945, filed Aug. 8, 2018, Wu.
U.S. Appl. No. 16/109,199, filed Aug. 22, 2018, Wu.
U.S. Appl. No. 16/043,821, filed Jul. 24, 2018, Ibrahim et al.
U.S. Appl. No. 16/123,612, filed Sep. 6, 2018, Desai et al.
U.S. Appl. No. 16/148,244, filed Oct. 1, 2018, Zhang et al.

Asai et al., "Depletion of microglia and inhibition of exosome synthesis halt tau propagation", Nature Neuroscience, 2015, vol. 18, No. 11, pp. 1584-1593.

(56) References Cited

OTHER PUBLICATIONS

Bosch et al., "Neuroinflammatory paradigms in lysosomal storage diseases", Frontiers in Neuroscience, 2015, vol. 9, Article 417. (11 pages).
Cheng et al., "High expression of FLT3 is a risk factor in leukemia", Molecular Medicine Reports, 2018, 17, pp. 2885-2892.
Cioce et al., "Autocrine CSF-1R signaling drives mesothelioma chemoresistance via AKT activation", Cell Death and Disease, 2014, 5, p. e1167.
Escamilla et al., "CSF1 Receptor Targeting in Prostate Cancer Reverses Macrophage-Mediated Resistance to Androgen Blockade Therapy", Cancer Res, 2015, 75(6), pp. 950-962.
Han et al., "An updated assessment of microglia depletion: current concepts and future directions", Molecular Brain, 2017, 10:25. (8 pages).
He et al., "c-Fms Signaling Mediates Neurofibromatosis Type-1 Osteoclast Gain-In-Functions", PLOS One, 2012, vol. 7, Issue 11, p. e46900.
Huang et al., "The possible mechanisms of tumor progression via CSF-1/CSF-1R pathway activation", Rom J Morphol Embryol, 2014, 55(2 Suppl), pp. 501-506.
International Preliminary Report on Patentability for International Application No. PCT/US2016/031027 dated Nov. 7, 2017. (6 pages).
International Search Report and Written Opinion for PCT/US2016/031027 dated Aug. 3, 2016, 11 pages.
Jia et al., "High Expression of Macrophage Colony-Stimulating Factor-1 Receptor in Peritumoral Liver Tissue Is Associated with Poor Outcome in Hepatocellular Carcinoma After Curative Resection", The Oncologist, 2010, 15. (13 pages).
Kacinski et al., "High level expression of fms proto-oncogene mRNA is observed in clinically aggressive human endometrial adenocarcinomas", International Journal of Radiation OncologyBiologyPhysics, 1988, vol. 15, Issue 4, pp. 823-829. Abstract.
Kamenz et al., "Expression of c-kit receptor in human cholangiocarcinoma and in vivo treatment with imatinib mesilate in chimeric mice", World J Gastroenterol, 2006, 12(10), pp. 1583-1590.
Knight et al., "Increased Microglial CSF1R Expression in the SIV/Macaque Model of HIV CNS Disease", Journal of Neuropathology & Experimental Neurology, vol. 77, Issue 3, 2018, pp. 199-206. Abstract.
Li et al., "Colony stimulating factor I receptor inhibition eliminates microglia and attenuates brain injury after intracerebral hemorrhage", Journal of Cerebral Blood Flow & Metabolism, 2017, 37(7), pp. 2383-2395.
Littlejohn, G., "Neurogenic neuroinflammation in fibromyalgia and complex regional pain syndrome." Nat Rev Rheumatol, 2015, 11(11), pp. 639-648. Abstract.
Mallard et al., "Astrocytes and microglia in acute cerebral injury underlying cerebral palsy associated with preterm birth", Pediatric Research, 2014, vol. 75, No. 1, pp. 234-240.
McCarron et al., Plexiform neurofibroma with and without associated malignant peripheral nerve sheath tumor: a clinicopathologic and immunohistochemical analysis of 54 cases. Mod Pathol. 1998, 11(7), pp. 612-617. Abstract.
Melao, A., "#MSParis2017—Inhibiting Protein in Brain Cells Can Rejuvenate Protective Nerve Cell Coating, Study Shows", Multiple Sclerosis News Today, 2017. (2 pages).
Menke et al., "Autocrine CSF-1 and CSF-1 Receptor Coexpression Promotes Renal Cell Carcinoma Growth", Cancer Res, 2011, 72(1), pp. 1-14.

Morandi et al., "The Colony-Stimulating Factor-1 (CSF-1) Receptor Sustains ERK1/2 Activation and Proliferation in Breast Cancer Cell Lines", PLoS One, 2011, vol. 6, Issue 11, p. e27450.
Moskowitz et al., "CSF1R Inhibition by PLX3397 in Patients with Relapsed or Refractory Hodgkin Lymphoma: Results From a Phase 2 Single Agent Clinical Trial", Blood, 2012, 120, p. 1638. Abstract.
Mughal, et al. Principal long-term adverse effects of imatinib in patients with chronic myeloid leukemia in chronic phase. Biologics. Dec. 2, 2010;4:315-23. doi: 10.2147/BTT.S5775.
Olmos-Alonso et al., "Pharmacological targeting of CSF1R inhibits microglial proliferation and prevents the progression of Alzheimer's-like pathology", Brain, 2016, 139, pp. 891-907.
Passamonti et al., "[11C]PK11195 PET in Alzheimer's disease and progressive supranuclear palsy: The NIMROD Study", 2017. (1 page).
Patwardhan et al., "Sustained inhibition of receptor tyrosine kinases and macrophage depletion by PLX3397 and rapamycin as a potential new approach for the treatment of MPNSTs", Clin Cancer Res., 2014, 20(12), pp. 3146-3158.
Pyonteck et al., "CSF-1R inhibition alters macrophage polarization and blocks glioma progression", Nat Med., 2013, 19(10), pp. 1264-1272.
Ries et al., "Targeting Tumor-Associated Macrophages with Anti-CSF-1R Antibody Reveals a Strategy for Cancer Therapy", Cancer Cell, 2014, 25, pp. 846-859.
Salehinejad J. et al., "Evaluation of c-kit protein (CD117) expression in common salivary gland neoplasms." J Oral Maxillofac Pathol, 2014, 18(2), pp. 177-182. Abstract.
Siehl, J. et al., "C-kit, GIST, and imatinib." Recent Results Cancer Res., 2007, 176, pp. 145-151. Abstract.
Sluijter et al., "Inhibition of CSF-1R Supports T-Cell Mediated Melanoma Therapy", PLOS One, 2014, vol. 9, Issue 8, p. e104230.
Spangenberg et al., "Eliminating microglia in Alzheimer's mice prevents neuronal loss without modulating amyloid-ß pathology", Brain, 2016, 139, pp. 1265-1281.
Srivastava et al., "A systems-level framework for drug discovery identifies CSF1R as a novel anti-epileptic drug target", bioRxiv preprint first posted online May 22, 2017.
Stefaniak et al., "Imaging of neuroinflammation in dementia: a review." J Neurol Neurosurg Psychiatry, 2016, 87(1), pp. 21-8. Abstract.
Tap, W.D., "Phase I Data Suggest PLX3397 Is a Potential Therapy for Patients with Advanced Pigmented Villonodular Synovitis", Pressroom/Press Releases, Memorial Sloan Kettering Cancer Center, 2014. (3 pages).
Terada et al., "Esophageal combined carcinomas: Immunohoistochemical and molecular genetic studies", World J Gastroenterol, 2012, 18(13), pp. 1545-1551.
Terry, M., Daiichi Sankyo's Tumor Drug Meets Primary Endpoint in Late-Stage Study. Published: Oct. 31, 2017. (3 pages).
Wei et al., "Regulation of Csf1r and Bcl6 in Macrophages Mediates the Stage-Specific Effects of MicroRNA-155 on Atherosclerosis", Arterioscler Thromb Vasc Biol, 2015, 35, pp. 796-803.
Williams et al., "Neuroinflammation in glaucoma: A new opportunity[1]", Exp Eye Res., 2017, 157, pp. 20-27.
Wong, W.T., "Immune cells in the retina can spontaneously regenerate", ScienceDaily, NIH/National Eye Institute, 2018. (5 pages).
Yu et al., "CSF-1R regulates non-small cell lung cancer cells dissemination through Wnt3a signaling", Am J Cancer Res 2017, 7(11), pp. 2144-2156.

* cited by examiner

FORMULATIONS OF A COMPOUND MODULATING KINASES

CROSS-REFERENCE TO RELATED APPLICATIONS

This application claims the benefit under 35 U.S.C. § 119(e) of U.S. Provisional Application 62/536,574, filed Jul. 25, 2017, which is hereby incorporated by reference in its entirety.

FIELD OF THE DISCLOSURE

Disclosed are new compositions of biologically active compounds that are useful for treating diseases, and methods of making such compositions.

BACKGROUND OF THE DISCLOSURE

CSF1R inhibitors are small molecule receptor tyrosine kinase inhibitor that targets CSF1R (the receptor for macrophage-colony stimulating factor). Compound I of this disclosure is known to inhibit CSF1R, c-Kit and FLT3.

There is a need for effective treatments for subjects suffering from or at risk of a c-Kit and/or c-Fms mediated disease or condition. Suitable compounds for the treatment of such diseases and conditions include Compound I of this disclosure that is disclosed in U.S. Pat. No. 7,893,075, U.S. Publication No. 2014-0037617 and U.S. Publication No. 2013-0274259, the disclosures of all of which is incorporated herein by reference in their entirety. However, effective formulations of Compound I were not known in any of the specific formulations described herein.

SUMMARY OF THE DISCLOSURE

Compositions of this disclosure can be used for oral administration to subjects for treating disease and conditions modulated by CSF1R, c-Kit, and/or FLT3. In certain embodiments, the compositions of this disclosure have improved dissolution profiles.

The present disclosure relates to compositions comprising Compound I having the following structure:

The present disclosure also relates to methods of making compositions of this disclosure which further improves the dissolution profiles of the compositions.

The present disclosure also relates to compositions made by the methods of this disclosure.

The present disclosure also relates to methods of treating subjects of a disease or condition mediated by CSF1R, c-Kit and/or FLT3, comprising administering any of the compositions of this disclosure to said subject.

Additional aspects and embodiments will be apparent from the following Detailed Description and from the claims.

DETAILED DESCRIPTION

Figure 1:
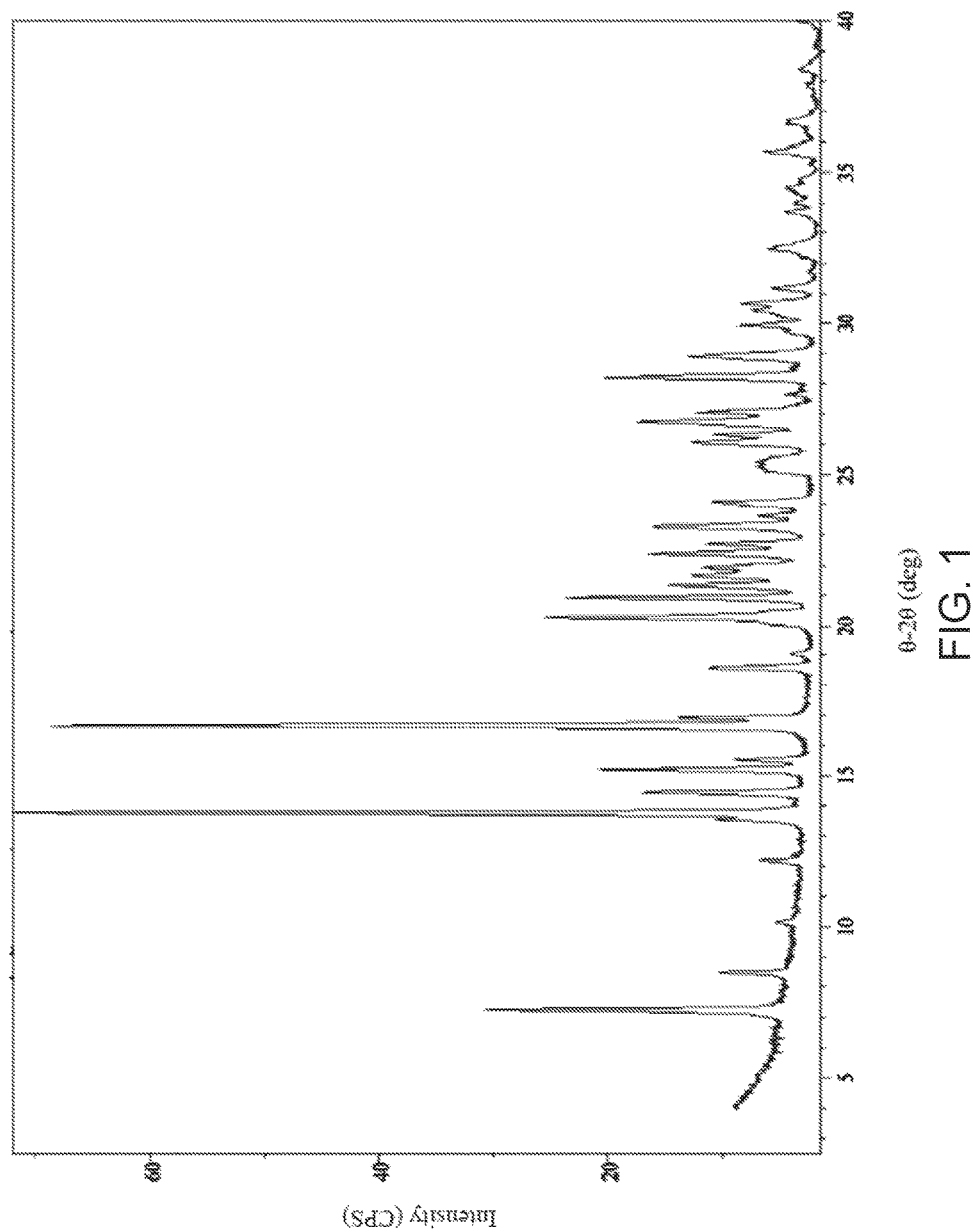
FIG. 1 is an X-ray powder diffraction pattern of Compound I Form C.

The disclosure provides compositions comprising Compound I, including pharmaceutically acceptable salts thereof. Compound I has the following structure:

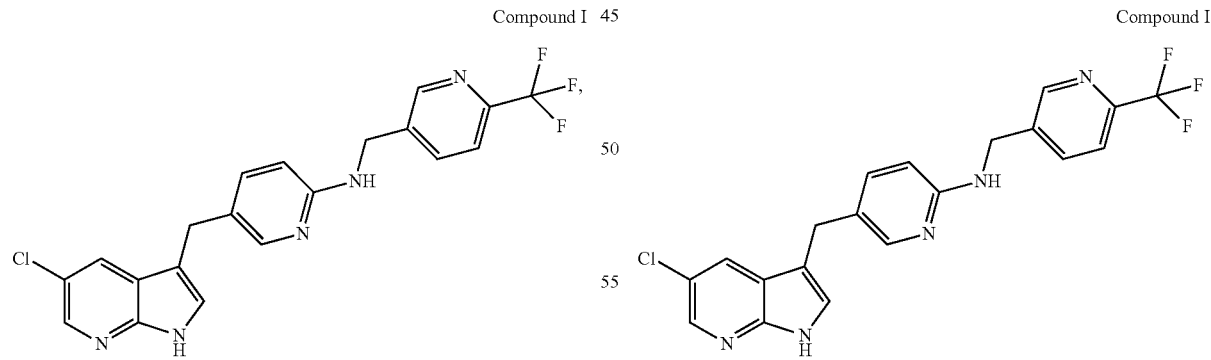

Compound I or a pharmaceutically acceptable salt thereof, and a solubilizing agent.

The compositions of this disclosure include compositions of crystal forms of Compound I, including Form C of Compound I as described in this disclosure.

In another embodiment, the compositions of this disclosure further comprise one or more excipients, a disintegrant, and a lubricant.

Compound I is also referred to as 5-(5-chloro-1H-pyrrolo[2,3-b]pyridin-3-ylmethyl)-pyridin-2-yl]-(6-trifluoromethyl-pyridin-3-ylmethyl)-amine, PLX3397, or pexidartinib. The present disclosure further provides compositions comprising crystalline forms of Compound I, including crystalline forms of pharmaceutically acceptable salts of Compound I. The present disclosure further provides compositions comprising crystalline forms of HCl salts of Compound I. The present disclosure further provides compositions comprising crystalline Form C of Compound I.

In other embodiments, a composition of this disclosure comprises Compound I, or a pharmaceutically acceptable salt thereof, and a solubilizing agent. In some embodiments, Compound I is an HCl salt of Compound I. In some embodiments, the HCl salt of Compound I is crystalline. In some embodiments, the crystalline HCl salt of Compound I is Form C.

In other embodiments, a composition of this disclosure comprises an HCl salt of Compound I and a solubilizing agent.

In other embodiments, a composition of this disclosure comprises a crystalline form of an HCl salt of Compound I and a solubilizing agent. In other embodiments, a composition of this disclosure comprises crystalline Form C of Compound I and a solubilizing agent.

In other embodiments, a composition of this disclosure comprises Compound I, or a pharmaceutically acceptable salt thereof, ranging from about 50% to about 75% W/W; and a solubilizing agent ranging from about 25% to about 50% W/W.

In other embodiments, a composition of this disclosure comprises an HCl salt of Compound I ranging from about 50% to about 75% W/W; and a solubilizing agent ranging from about 25% to about 50% W/W.

In other embodiments, a composition of this disclosure comprises a crystalline form of an HCl salt of Compound I ranging from about 50% to about 75% W/W; and a solubilizing agent ranging from about 25% to about 50% W/W.

In other embodiments, a composition of this disclosure comprises Form C of Compound I ranging from about 50% to about 75% W/W; and a solubilizing agent ranging from about 25% to about 50% W/W.

In other embodiments, a composition of this disclosure comprises Compound I, or a pharmaceutically acceptable salt thereof, ranging from about 60% to about 70% W/W; and a solubilizing agent ranging from about 30% to about 40% W/W.

In other embodiments, a composition of this disclosure comprises an HCl salt of Compound I ranging from about 60% to about 70% W/W; and a solubilizing agent ranging from about 30% to about 40% W/W.

In other embodiments, a composition of this disclosure comprises a crystalline form of an HCl salt of Compound I ranging from about 60% to about 70% W/W; and a solubilizing agent ranging from about 30% to about 40% W/W.

In other embodiments, a composition of this disclosure comprises Form C of Compound I ranging from about 60% to about 70% W/W; and a solubilizing agent ranging from about 30% to about 40% W/W.

In other embodiments, a composition of this disclosure comprises Compound I, or a pharmaceutically acceptable salt thereof, ranging from about 63% to about 67% W/W; and a solubilizing agent ranging from about 33% to about 37% W/W.

In other embodiments, a composition of this disclosure comprises an HCl salt of Compound I ranging from about 63% to about 67% W/W; and a solubilizing agent ranging from about 33% to about 37% W/W.

In other embodiments, a composition of this disclosure comprises a crystalline form of the HCl salt of Compound I ranging from about 63% to about 67% W/W; and a solubilizing agent ranging from about 33% to about 37% W/W.

In other embodiments, a composition of this disclosure comprises Form C of Compound I ranging from about 63% to about 67% W/W; and a solubilizing agent ranging from about 33% to about 37% W/W.

In other embodiments, a composition of this disclosure comprises Compound I, or a pharmaceutically acceptable salt thereof, at about 65% W/W; and a solubilizing agent at about 35% W/W.

In other embodiments, a composition of this disclosure comprises an HCl salt of Compound I at about 65% W/W; and a solubilizing agent at about 35% W/W.

In other embodiments, a composition of this disclosure comprises a crystalline form of an HCl salt of Compound I at about 65% W/W; and a solubilizing agent at about 35% W/W.

In other embodiments, a composition of this disclosure comprises Form C of Compound I at about 65% W/W; and a solubilizing agent at about 35% W/W.

The crystalline Form C of Compound I (also referred to as "Compound I Form C" or "Form C"), within any of the compositions of this disclosure, is characterized by an X-ray powder diffractogram comprising peaks (±0.2°) at 7.3, 23.3 and 28.2° 2θ as determined on a diffractometer using Cu-Kα radiation. In another embodiment, Compound I Form C, within any of the compositions of this disclosure, further comprises peaks at 16.6 and 20.9°2θ±0.2°.

Figure 2:
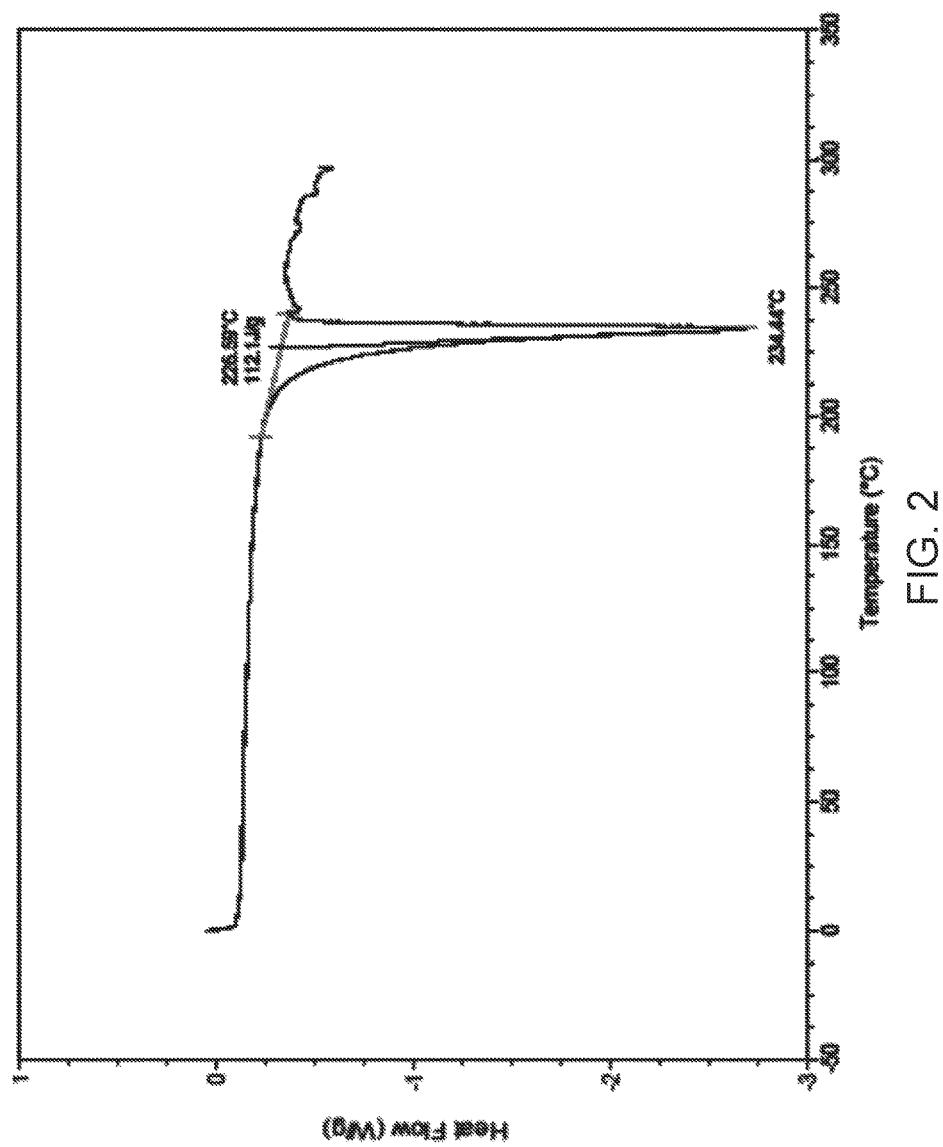
FIG. 2 is differential scanning calorimetry (DSC) curve of Compound I Form C.
Figure 3:
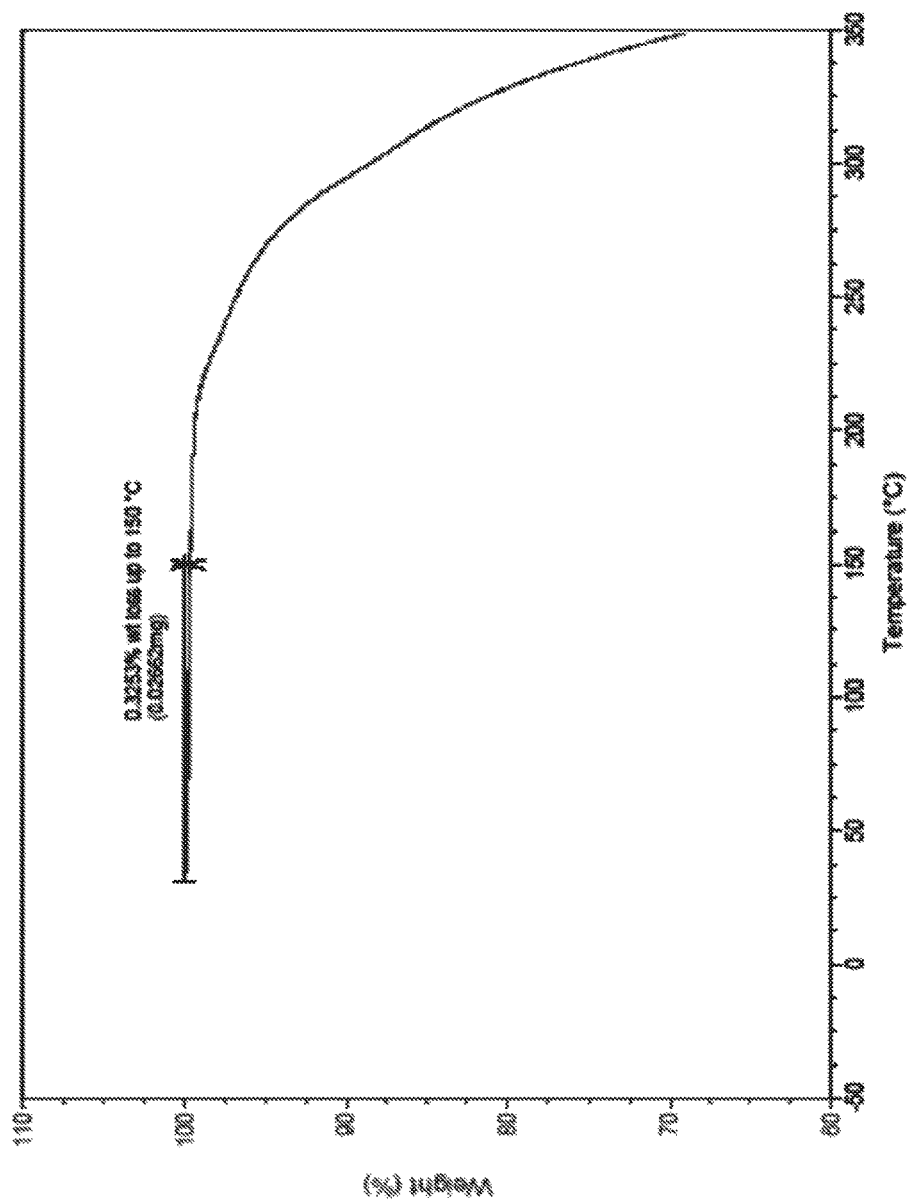
FIG. 3 is thermogravimetric analysis (TGA) of Compound I Form C.
Figure 4:
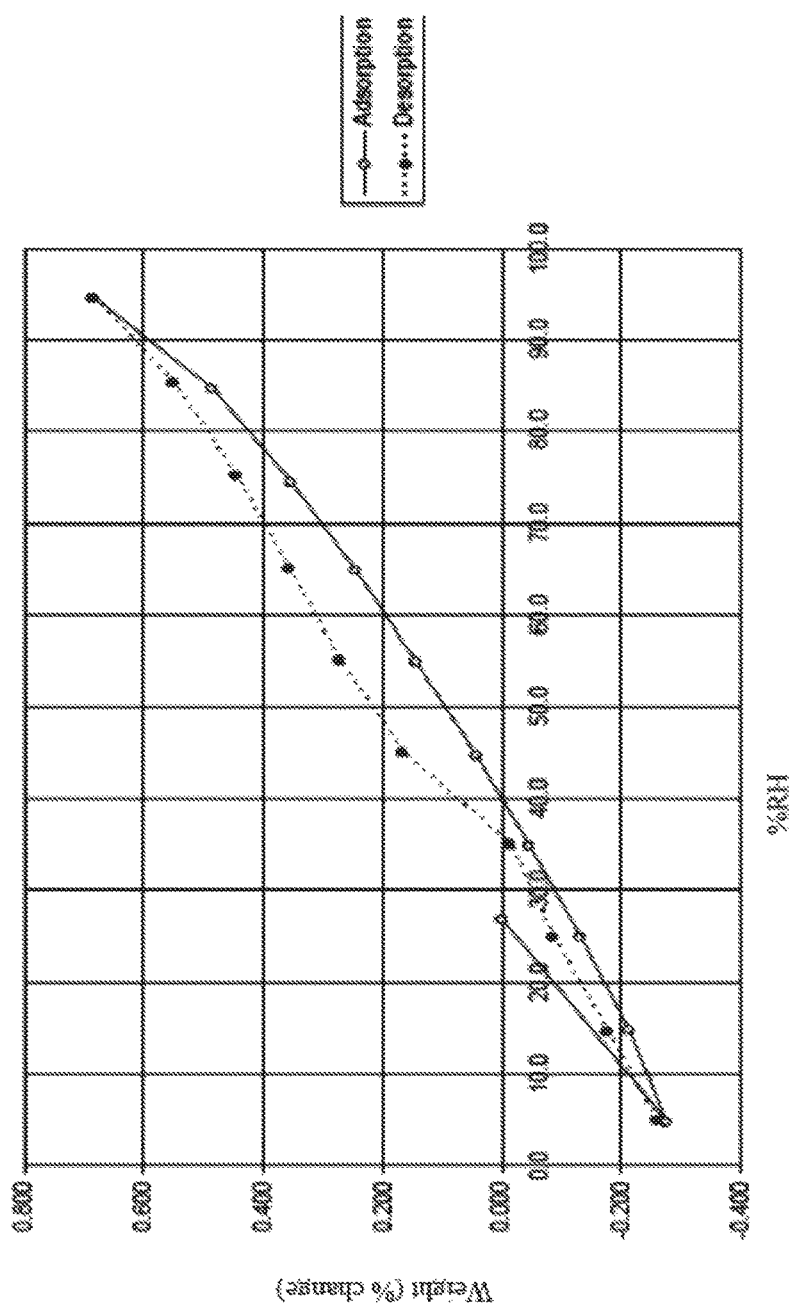
FIG. 4 is dynamic vapor sorption (DVS) curve of Compound I Form C.

In other embodiments, Compound I Form C, within any of the compositions of this disclosure is characterized by:
i) a diffractogram substantially as shown in FIG. 1;
ii) a differential scanning calorimetry (DSC) thermogram comprising an endotherm at about 234° C.;
iii) a DSC thermogram substantially as shown in FIG. 2;
iv) thermogravimetric analysis (TGA) comprising a thermogram substantially as shown in FIG. 3; or
v) a dynamic vapor sorption (DVS) curve substantially as shown in FIG. 4.

Compound I Form C is described in WO 2016/179415, the contents of which are incorporated herein-by-reference in its entirety.

A non-limiting example of a solubilizing agent that can be used in the compositions of this disclosure include a poloxamer. Poloxamer is available in different grades. Examples of available grades include poloxamer (68, 88, 98, 108, 124, 188, 237, 338, and 407). Poloxamer is commercially available. In some embodiments, the solubilizing agent is a poloxamer. In some embodiments, the poloxamer is poloxamer 407.

In other embodiments of disclosure, a composition disclosed herein comprises Compound I, or a pharmaceutically acceptable salt thereof, and poloxamer 407. In other embodiments of this disclosure, a composition disclosed herein comprises an HCl salt of Compound I and poloxamer 407. In other embodiments, a composition of this disclosure comprises a crystalline form of an HCl salt of Compound I and poloxamer 407. In other embodiments, a composition of this disclosure comprises crystalline Form C of Compound I and poloxamer 407. Poloxamer 407 is commercially available.

In other embodiments, a composition of this disclosure comprises Compound I, or a pharmaceutically acceptable salt thereof, wherein Compound I, or a pharmaceutically acceptable salt thereof, is Form C, and Form C ranges from 60% to about 70% W/W; and a solubilizing agent, wherein the solubilizing agent is poloxamer 407, and poloxamer 407 ranges from about 30% to about 40% W/W.

In other embodiments, a composition of this disclosure comprises Compound I, or a pharmaceutically acceptable salt thereof, ranging from about 50% to about 75% W/W; and poloxamer 407 ranging from about 25% to about 50% W/W.

In other embodiments, a composition of this disclosure comprises an HCl salt of Compound I ranging from about 50% to about 75% W/W; and poloxamer 407 ranging from about 25% to about 50% W/W.

In other embodiments, a composition of this disclosure comprises a crystalline form of an HCl salt of Compound I ranging from about 50% to about 75% W/W; and poloxamer 407 ranging from about 25% to about 50% W/W.

In other embodiments, a composition of this disclosure comprises Form C of Compound I ranging from about 50% to about 75% W/W; and poloxamer 407 ranging from about 30% to about 40% W/W.

In other embodiments, a composition of this disclosure comprises Compound I, or a pharmaceutically acceptable salt thereof, ranging from about 60% to about 70% W/W; and poloxamer 407 ranging from about 30% to about 40% W/W.

In other embodiments, a composition of this disclosure comprises an HCl salt of Compound I ranging from about 60% to about 70% W/W; and poloxamer 407 ranging from about 30% to about 40% W/W.

In other embodiments, a composition of this disclosure comprises a crystalline form of an HCl salt of Compound I ranging from about 60% to about 70% W/W; and poloxamer 407 ranging from about 30% to about 40% W/W.

In other embodiments, a composition of this disclosure comprises Form C of Compound I ranging from about 60% to about 70% W/W; and poloxamer 407 ranging from about 30% to about 40% W/W.

In other embodiments, a composition of this disclosure comprises Compound I, or a pharmaceutically acceptable salt thereof, ranging from about 63% to about 67% W/W; and poloxamer 407 ranging from about 33% to about 37% W/W.

In other embodiments, a composition of this disclosure comprises an HCl salt of Compound I ranging from about 63% to about 67% W/W; and poloxamer 407 ranging from about 33% to about 37% W/W.

In other embodiments, a composition of this disclosure comprises a crystalline form of an HCl salt of Compound I ranging from about 63% to about 67% W/W; and poloxamer 407 ranging from about 33% to about 37% W/W.

In other embodiments, a composition of this disclosure comprises Form C of Compound I ranging from about 63% to about 67% W/W; and poloxamer 407 ranging from about 33% to about 37% W/W.

In other embodiments, a composition of this disclosure comprises Compound I, or a pharmaceutically acceptable salt thereof, at about 65% W/W; and poloxamer 407 at about 35% W/W.

In other embodiments, a composition of this disclosure comprises an HCl salt of Compound I at about 65% W/W; and poloxamer 407 at about 35% W/W.

In other embodiments, a composition of this disclosure comprises a crystalline form of an HCl salt of Compound I at about 65% W/W; and poloxamer 407 at about 35% W/W.

In other embodiments, a composition of this disclosure comprises Form C of Compound I at about 65% W/W; and poloxamer 407 at about 35% W/W.

In other embodiments, a composition of this disclosure comprises Compound I, or a pharmaceutically acceptable salt thereof, a solubilizing agent, an excipient, a disintegrant, and a lubricant. In other embodiments, a composition of this disclosure comprises an HCl salt of Compound I, a solubilizing agent, an excipient, a disintegrant, and a lubricant. In other embodiments, a composition of this disclosure comprises a crystalline form of an HCl salt of Compound I, a solubilizing agent, an excipient, a disintegrant, and a lubricant. In other embodiments, a composition of this disclosure comprises crystalline Form C of Compound I, a solubilizing agent, an excipient, a disintegrant, and a lubricant.

In other embodiments, a composition of this disclosure comprises Compound I, or a pharmaceutically acceptable salt thereof, a solubilizing agent, one or more excipients, a disintegrant, and a lubricant. In other embodiments, a composition of this disclosure comprises an HCl salt of Compound I, a solubilizing agent, one or more excipients, a disintegrant, and a lubricant. In other embodiments, a composition of this disclosure comprises a crystalline form of an HCl salt of Compound I, a solubilizing agent, one or more excipients, a disintegrant, and a lubricant. In other embodiments, a composition of this disclosure comprises crystalline Form C of Compound I, a solubilizing agent, one or more excipients, a disintegrant, and a lubricant.

In other embodiments, a composition of this disclosure comprises Compound I, or a pharmaceutically acceptable salt thereof, a solubilizing agent, two excipients, a disintegrant, and a lubricant. In other embodiments, a composition of this disclosure comprises an HCl salt of Compound I, a solubilizing agent, two excipients, a disintegrant, and a lubricant. In other embodiments, a composition of this disclosure comprises a crystalline form of an HCl salt of Compound I, a solubilizing agent, two excipients, a disintegrant, and a lubricant. In other embodiments, a composition of this disclosure comprises crystalline Form C of Compound I, a solubilizing agent, two excipients, a disintegrant, and a lubricant.

In other embodiments, a composition of this disclosure comprises Compound I, or a pharmaceutically acceptable salt thereof, ranging from about 40% to about 60% W/W; a solubilizing agent ranging from about 20% to about 35% W/W; an excipient ranging from about 10% to about 22% W/W; a disintegrant ranging from about 1% to about 5% W/W; and a lubricant ranging from about 0.5% to about 3% W/W.

In other embodiments, a composition of this disclosure comprises Compound I, or a pharmaceutically acceptable salt thereof, ranging from about 45% to about 55% W/W; a solubilizing agent ranging from about 24% to about 32% W/W; an excipient ranging from about 14% to about 20% W/W; a disintegrant ranging from about 2% to about 4% W/W; and a lubricant ranging from about 1.0% to about 2.5% W/W.

In other embodiments, a composition of this disclosure comprises Compound I, or a pharmaceutically acceptable salt thereof, ranging from about 48% to about 53% W/W; a solubilizing agent ranging from about 26% to about 29% W/W; an excipient ranging from about 15% to about 18% W/W; a disintegrant ranging from about 2.5% to about 3.5% W/W; and a lubricant ranging from about 1.2% to about 1.8% W/W.

In other embodiments, a composition of this disclosure comprises Compound I, or a pharmaceutically acceptable salt thereof, at about 51.2% W/W; a solubilizing agent at about 27.6% W/W; an excipient at 16.8% W/W; a disintegrant at 3.0% W/W; and a lubricant at 1.5% W/W.

In other embodiments, a composition of this disclosure comprises an HCl salt of Compound I ranging from about 40% to about 60% W/W; a solubilizing agent ranging from about 20% to about 35% W/W; an excipient ranging from about 10% to about 22% W/W; a disintegrant ranging from about 1% to about 5% W/W; and a lubricant ranging from about 0.5% to about 3% W/W.

In other embodiments, a composition of this disclosure comprises a crystalline form of the HCl salt of Compound I ranging from about 45% to about 55% W/W; a solubilizing agent ranging from about 24% to about 32% W/W; an excipient ranging from about 14% to about 20% W/W; a disintegrant ranging from about 2% to about 4% W/W; and a lubricant ranging from about 1.0% to about 2.5% W/W.

In other embodiments, a composition of this disclosure comprises Form C of Compound I ranging from about 48% to about 53% W/W; a solubilizing agent ranging from about 26% to about 29% W/W; an excipient ranging from about 15% to about 18% W/W; a disintegrant ranging from about 2.5% to about 3.5% W/W; and a lubricant ranging from about 1.2% to about 1.8% W/W.

Non-limiting examples of excipients that can be used in the compositions of this disclosure include microcrystalline cellulose, mannitol, sorbitol, maltodextrin, maltose, dextrin, dibasic calcium phosphate dihydrate, dibasic calcium phosphate anhydrate, partially pregelatinized starch, and tribasic calcium phosphate, and the like, or mixtures thereof. In certain embodiments, compositions of this disclosure contain both microcrystalline cellulose and mannitol as excipients. In other embodiments, the compositions of this disclosure contain mannitol as the excipient. All aforementioned excipients are commercially available.

Non-limiting examples of disintegrants that can be used in the compositions of this disclosure include sodium starch glycolate, croscarmellose sodium, crospovidone, and the like, or mixtures thereof. In other embodiments, the compositions of this disclosure contain crospovidone as the disintegrant. In other embodiments of this disclosure, the crospovidone is Polyplasdone® Ultra or Polyplasdone® Ultra-10, Polyplasdone® XL, or Polyplasdone® XL-10. In other embodiments of this disclosure, the crospovidone is Polyplasdone® Ultra or Polyplasdone® Ultra-10. All aforementioned disintegrants are commercially available.

Non-limiting examples of lubricants that can be used in the compositions of this disclosure include magnesium stearate, stearic acid, palmitic acid, calcium stearate, carnauba wax, hydrogenated vegetable oils, mineral oil, polyethylene glycols, sodium stearyl fumarate, and the like, or mixtures thereof. In one aspect, the lubricant is magnesium stearate or sodium stearyl fumarate. In other embodiments, the compositions of this disclosure contain magnesium stearate as the lubricant. All aforementioned lubricants are commercially available.

It will be understood that a particular excipient may act as a diluent, a filler, or a disintegrant.

In some embodiments, the solubilizing agent is poloxamer; the excipient is mannitol; the disintegrant is crospovidone; and the lubricant is magnesium stearate. In some embodiments, the solubilizing agent is poloxamer 407; the excipient is mannitol; the disintegrant is crospovidone; and the lubricant is magnesium stearate.

In other embodiments, a composition of this disclosure comprises Compound I, or a pharmaceutically acceptable salt thereof, poloxamer 407, microcrystalline cellulose, mannitol, crospovidone, and magnesium stearate. In other embodiments, a composition of this disclosure comprises an HCl salt of Compound I, poloxamer 407, microcrystalline cellulose, mannitol, crospovidone, and magnesium stearate. In other embodiments, a composition of this disclosure comprises a crystalline form of an HCl salt of Compound I, poloxamer 407, microcrystalline cellulose, mannitol, crospovidone, and magnesium stearate. In other embodiments, a composition of this disclosure comprises crystalline Form C of Compound I, poloxamer 407, microcrystalline cellulose, mannitol, crospovidone, and magnesium stearate.

In other embodiments, a composition of this disclosure comprises Compound I, or a pharmaceutically acceptable salt thereof, poloxamer 407, mannitol, crospovidone, and magnesium stearate. In other embodiments, a composition of this disclosure comprises an HCl salt of Compound I, poloxamer 407, mannitol, crospovidone, and magnesium stearate. In other embodiments, a composition of this disclosure comprises a crystalline form of an HCl salt of Compound I, poloxamer 407, mannitol, crospovidone, and magnesium stearate. In other embodiments, a composition of this disclosure comprises crystalline Form C of Compound I, poloxamer 407, mannitol, crospovidone, and magnesium stearate.

In other embodiments, a composition of this disclosure comprises Compound I, or a pharmaceutically acceptable salt thereof, ranging from about 40% to about 60% W/W; poloxamer 407 ranging from about 20% to about 35% W/W; mannitol ranging from about 10% to about 22% W/W; crospovidone ranging from about 1% to about 5% W/W; and magnesium stearate ranging from about 0.5% to about 3% W/W.

In other embodiments, a composition of this disclosure comprises an HCl salt of Compound I ranging from about 40% to about 60% W/W; poloxamer 407 ranging from about 20% to about 35% W/W; mannitol ranging from about 10% to about 22% W/W; crospovidone ranging from about 1% to about 5% W/W; and magnesium stearate ranging from about 0.5% to about 3% W/W.

In other embodiments, a composition of this disclosure comprises an crystalline HCl salt of Compound I ranging from about 40% to about 60% W/W; poloxamer 407 ranging from about 20% to about 35% W/W; mannitol ranging from about 10% to about 22% W/W; crospovidone ranging from about 1% to about 5% W/W; and magnesium stearate ranging from about 0.5% to about 3% W/W.

In other embodiments, a composition of this disclosure comprises Compound I Form C ranging from about 40% to about 60% W/W; poloxamer 407 ranging from about 20% to about 35% W/W; mannitol ranging from about 10% to about 22% W/W; crospovidone ranging from about 1% to about 5% W/W; and magnesium stearate ranging from about 0.5% to about 3% W/W.

In other embodiments, a composition of this disclosure comprises Compound I, or a pharmaceutically acceptable salt thereof, ranging from about 45% to about 55% W/W; poloxamer 407 ranging from about 24% to about 32% W/W; mannitol ranging from about 14% to about 20% W/W; crospovidone ranging from about 2% to about 4% W/W; and magnesium stearate ranging from about 1.0% to about 2.5% W/W.

In other embodiments, a composition of this disclosure comprises an HCl salt of Compound I ranging from about 45% to about 55% W/W; poloxamer 407 ranging from about 24% to about 32% W/W; mannitol ranging from about 14% to about 20% W/W; crospovidone ranging from about 2% to about 4% W/W; and magnesium stearate ranging from about 1.0% to about 2.5% W/W.

In other embodiments, a composition of this disclosure comprises a crystalline form of an HCl salt of Compound I ranging from about 45% to about 55% W/W; poloxamer 407 ranging from about 24% to about 32% W/W; mannitol ranging from about 14% to about 20% W/W; crospovidone ranging from about 2% to about 4% W/W; and magnesium stearate ranging from about 1.0% to about 2.5% W/W.

In other embodiments, a composition of this disclosure comprises Compound I Form C ranging from about 45% to about 55% W/W; poloxamer 407 ranging from about 24% to about 32% W/W; mannitol ranging from about 14% to about 20% W/W; crospovidone ranging from about 2% to about 4% W/W; and magnesium stearate ranging from about 1.0% to about 2.5% W/W.

In other embodiments, a composition of this disclosure comprises Compound I, or a pharmaceutically acceptable salt thereof, ranging from about 48% to about 53% W/W; poloxamer 407 ranging from about 26% to about 29% W/W; mannitol ranging from about 15% to about 18% W/W; crospovidone ranging from about 2.5% to about 3.5% W/W; and magnesium stearate ranging from about 1.2% to about 1.8% W/W.

In other embodiments, a composition of this disclosure comprises an HCl salt of Compound I ranging from about 48% to about 53% W/W; poloxamer 407 ranging from about 26% to about 29% W/W; mannitol ranging from about 15% to about 18% W/W; crospovidone ranging from about 2.5% to about 3.5% W/W; and magnesium stearate ranging from about 1.2% to about 1.8% W/W.

In other embodiments, a composition of this disclosure comprises crystalline form of an HCl salt of Compound I ranging from about 48% to about 53% W/W; poloxamer 407 ranging from about 26% to about 29% W/W; mannitol ranging from about 15% to about 18% W/W; crospovidone ranging from about 2.5% to about 3.5% W/W; and magnesium stearate ranging from about 1.2% to about 1.8% W/W.

In other embodiments, a composition of this disclosure comprises Form C of Compound I ranging from about 48% to about 53% W/W; poloxamer 407 ranging from about 26% to about 29% W/W; mannitol ranging from about 15% to about 18% W/W; crospovidone ranging from about 2.5% to about 3.5% W/W; and magnesium stearate ranging from about 1.2% to about 1.8% W/W.

In other embodiments, a composition of this disclosure comprises Compound I, or a pharmaceutically acceptable salt thereof, at about 51.2% W/W; poloxamer 407 at about 27.6% W/W; mannitol at about 16.8% W/W; crospovidone at about 3% W/W; and magnesium stearate at about 1.5% W/W.

In another embodiment, a composition of this disclosure comprises an HCl salt of Compound I at about 51.2% W/W; poloxamer 407 at about 27.6% W/W; mannitol at about 16.8% W/W; crospovidone at about 3% W/W; and magnesium stearate at about 1.5% W/W.

In another embodiment, a composition of this disclosure comprises a crystalline form of an HCl salt of Compound I at about 51.2% W/W; poloxamer 407 at about 27.6% W/W; mannitol at about 16.8% W/W; crospovidone at about 3% W/W; and magnesium stearate at about 1.5% W/W.

In another embodiment, a composition of this disclosure comprises Form C of Compound I at about 51.2% W/W; poloxamer 407 at about 27.6% W/W; mannitol at about 16.8% W/W; crospovidone at about 3% W/W; and magnesium stearate at about 1.5% W/W.

In other embodiments of this disclosure, the crospovidone in any of the compositions described herein is Polyplasdone® Ultra, Polyplasdone® Ultra-10, Polyplasdone® XL, or Polyplasdone® XL-10. In other embodiments of this disclosure, the crospovidone in any of the compositions described herein is Polyplasdone® Ultra or Polyplasdone® Ultra-10. In other embodiments of this disclosure, the crospovidone in any of the compositions described herein is Polyplasdone® Ultra. In other embodiments of this disclosure, the crospovidone in any of the compositions described herein is Polyplasdone® Ultra-10.

Methods of Preparing Compositions

Other embodiments of this disclosure relate to methods of preparing the compositions of this disclosure.

Methods for Preparing Compositions Comprising Compound I, or a Pharmaceutically Acceptable Salt Thereof, and a Solubilizing Agent.

In one embodiment, a method of preparing a composition of this disclosure comprises mixing Compound I, or a pharmaceutically acceptable salt thereof, and a solubilizing agent. Non-limiting examples of mixing equipment that can be used in preparing the compositions of this disclosure include a diffusion mixer (for example, V-blender or bin-blender) or a convection mixer (for example, a vertical high intensity mixer). Another embodiment of this disclosure relates to a composition prepared by this method.

In another embodiment, a method of preparing a composition of this disclosure comprises mixing Compound I, or a pharmaceutically acceptable salt thereof, and a solubilizing agent in a diffusion mixer. In another embodiment, a method of preparing a composition of this disclosure comprises mixing Compound I, or a pharmaceutically acceptable salt thereof, and a solubilizing agent in a convention mixer. In another embodiment, a method of preparing a composition of this disclosure comprises mixing Compound I, or a pharmaceutically acceptable salt thereof, and a solubilizing agent in a vertical high intensity mixer. In another embodiment, a method of preparing a composition of this disclosure comprises mixing Compound I, or a pharmaceutically acceptable salt thereof, and a solubilizing agent in a V-blender. In another embodiment, a method of preparing a composition of this disclosure comprises mixing Compound I, or a pharmaceutically acceptable salt thereof, and a solubilizing agent in a bin-blender. In a further embodiment of this method, Compound I, or a pharmaceutically acceptable salt thereof, is an HCl salt of Compound I. In a further embodiment of this method, Compound I, or a pharmaceutically acceptable salt thereof, is a crystalline form of an HCl salt of Compound I. In even a further embodiment of this method, Compound I, or a pharmaceutically acceptable salt thereof, is Form C of Compound I. Another embodiment of this disclosure relates a composition prepared by this method.

Methods for Preparing Compositions Comprising Compound I, or a Pharmaceutically Acceptable Salt Thereof, a Solubilizing Agent, an Excipient, A Disintegrant, and a Lubricant.

In another embodiment, a method of preparing a composition of this disclosure comprises (1) mixing Compound I, or a pharmaceutically acceptable salt thereof, and a solubilizing agent to provide a mixture; (2) roller-compacting the resulting mixture from (1) to provide roller-compacted ribbons; (3) milling the roller-compacted ribbons to provide granules; (4) blending the granules from (3), an excipient and a disintegrant; and (5) blending the mixture from (4) and a lubricant to provide a final blend. In a further embodiment of this method, Compound I, or a pharmaceutically acceptable salt thereof, is an HCl salt of Compound I. In a further embodiment of this method, Compound I, or a pharmaceutically acceptable salt thereof, is a crystalline form of an HCl salt of Compound I. In even a further embodiment of this method, Compound I, or a pharmaceutically acceptable salt thereof, is Form C of Compound I. Another embodiment of this disclosure relates to a composition prepared by this method.

Non-limiting examples of mixing equipment that can be used in preparing the compositions of this disclosure include a diffusion mixer (for example, V-blender or bin-blender) or a convection mixer (for example, a vertical high intensity mixer). Non-limiting examples of roller-compaction equipment that can be used in preparing the compositions of this disclosure include a dry granulator (for example, a roller compactor). Non-limiting examples of milling equipment that can be used in preparing the compositions of this disclosure include screening mills and cutting mills. Non-limiting examples of blending equipment that can be used in preparing the compositions of this disclosure include a diffusion mixer (for example, V-blender or bin-blender).

In another embodiment, a method of preparing a composition of this disclosure comprises (1) mixing Compound I, or a pharmaceutically acceptable salt thereof, and a solubilizing agent in a diffusion mixer to provide a mixture; (2) roller-compacting the resulting mixture from (1) in a dry granulator to provide roller-compacted ribbons; (3) milling the roller-compacted ribbons with cutting mills to provide granules; (4) blending the granules from (3), an excipient and a disintegrant with a diffusion mixer; and (5) blending the mixture from (4) and a lubricant with a diffusion mixer to provide a final blend. In a further embodiment of this method, Compound I, or a pharmaceutically acceptable salt thereof, is an HCl salt of Compound I. In a further embodiment of this method, Compound I, or a pharmaceutically acceptable salt thereof, is a crystalline form of an HCl salt of Compound I. In a further embodiment of this method, Compound I, or a pharmaceutically acceptable salt thereof, is Form C of Compound I. In a further embodiment of this method, the diffusion mixer is a V-blender. In yet a further embodiment of this method, the diffusion mixer is a bin-blender. In a further embodiment of this method, the roller compaction equipment is a dry granulator. In yet a further embodiment of this method, the milling equipment is a cutting mill. In yet a further embodiment of this method, Compound I, or a pharmaceutically acceptable salt thereof, is Form C of Compound I; the diffusion mixer is a bin-blender; the roller compaction equipment is a dry granulator; and the milling equipment is a cutting mill. Another embodiment of this disclosure relates to a composition prepared by this method.

In another embodiment, a method of preparing a composition of this disclosure comprises (1) mixing Compound I, or a pharmaceutically acceptable salt thereof, and a solubilizing agent in a convection mixer to provide a mixture; (2) roller-compacting the resulting mixture from (1) in a dry granulator to provide roller-compacted ribbons; (3) milling the roller-compacted ribbons with screening mills or cutting mills to provide granules; (4) blending the granules from (3), an excipient, and a disintegrant with a diffusion mixer; and (5) blending the mixture from (4) and a lubricant with a diffusion mixer to provide a final blend. In a further embodiment of this method, Compound I, or a pharmaceutically acceptable salt thereof, is an HCl salt of Compound I. In a further embodiment of this method, Compound I, or a pharmaceutically acceptable salt thereof, is a crystalline form of an HCl salt of Compound I. In a further embodiment of this method, Compound I, or a pharmaceutically acceptable salt thereof, is Form C of Compound I. In a further embodiment of this method, the convection mixer is a vertical high intensity mixer. In a further embodiment of this method, the roller compaction equipment is a dry granulator (roller compaction). In a further embodiment of this method, the milling equipment is a cutting mill or a screening mill. In another embodiment of this method, the mixing in (1) employs a diffusion mixer; the roller compacting in (2) employs a dry granulator to provide roller-compacted ribbons; the milling in (3) employs screening mills or cutting mills; the blending in (4) employs a diffusion mixer; and the blending in (5) employs a diffusion mixer. In another embodiment of this method, the mixing in (1) employs a convection mixer; the roller compacting in (2) employs a dry granulator to provide roller-compacted ribbons; the milling in (3) employs screening mills or cutting mills; the blending in (4) employs a diffusion mixer; and the blending in (5) employs a diffusion mixer. In yet a further embodiment of this method, Compound I, or a pharmaceutically acceptable salt thereof, is Form C of Compound I; the convection mixer is a vertical high intensity mixer; the roller compaction equipment is a dry granulator (roller compaction); and the milling equipment is a cutting mill or screening mill. Another embodiment of this disclosure relates to a composition prepared by this method.

In another embodiment of the method of preparing a composition of this disclosure, the milling comprises passing the roller compacted ribbons through a screening mill and an impeller rotation speed to provide granules. In another embodiment of the method of preparing a composition of this disclosure, the milling comprises passing the roller compacted ribbons through a cutting mill to provide granules.

Formulations

In other embodiments, any of the compositions of this disclosure is a formulation in a solid dosage form suitable for oral administration, such as a tablet (tablet formulation) or capsule (capsule formulation). In other embodiments, any of the compositions of this disclosure is in a solid dosage form of a capsule. In other embodiments, any of the compositions of this disclosure is in the form of a capsule comprising hard gelatin or hypromellose (HPMC). In other embodiments, any of the compositions of this disclosure is a formulation in the form of a capsule comprising hard gelatine. In other embodiments, any of the compositions of this disclosure is a formulation in the form of a capsule comprising hypromellose. In other embodiments, any of the compositions of this disclosure is a formulation suitable for administration to the eye, including, but not limited to, eye drops.

In other embodiments, any of the compositions of this disclosure is in a capsule form suitable for oral dosage. In other embodiments, any of the compositions of this disclosure is in the form of a capsule comprising hard gelatin or hypromellose, wherein the capsule contains a total of about 100 mg to about 200 mg of the ingredients in said compositions. In other embodiments, any of the compositions of this disclosure is in the form of a capsule comprising hard gelatine, wherein the capsule contains a total of about 100 mg to about 200 mg of the ingredients in said compositions. In other embodiments, any of the compositions of this disclosure is in the form of a capsule comprising hypromellose, wherein the capsule contains a total of about 100 mg to about 200 mg of the ingredients in said compositions.

In other embodiments, any of the compositions of this disclosure is in the form of a capsule comprising hard gelatin or hypromellose, wherein the capsule contains a total of about 100 mg of the ingredients in said compositions. In other embodiments, any of the compositions of this disclosure is in the form of a capsule comprising hard gelatine, wherein the capsule contains a total of about 100 mg of the ingredients in said compositions. In other embodiments, any of the compositions of this disclosure is in the form of a capsule comprising hypromellose, wherein the capsule contains a total of about 100 mg of the ingredients in said compositions.

Capsules comprising the compositions of this disclosure, wherein the disintegrant was Polyplasdone® Ultra or Polyplasdone® Ultra-10, had better stability than Polyplasdone® XL or Polyplasdone® XL-10.

In other embodiments, a composition of this disclosure comprises Compound I, or a pharmaceutically acceptable salt thereof, and a carrier. In other embodiments, a composition of this disclosure comprises an HCl salt of Compound I and a carrier. As used herein, the term "carrier" is meant to include microspheres, liposomes, micelles, nanoparticles (naturally-equipped nanocarriers, for example, exosomes), and the like. It is known that exosomes can be highly effective drug carriers, and there are various ways in which drugs can be loaded into exosomes, including those techniques described in J Control Release. 2015 Dec. 10; 219: 396-405, the contents of which are incorporated by reference in its entirety.

Methods of Treatment

In some embodiments, the disclosure provides a method for treating a disease or condition in a subject in need thereof, by administering to the subject a therapeutically effective amount of any of the compositions described herein.

The following describes various utilities of a compound that can inhibit one or more of Fms (CSF-1R or CSF1R), Flt-3 and Kit. Therefore, it is contemplated that Compound I, which inhibits Fms (CSF-1R or CSF1R), Flt-3 and Kit, can be used to treat the following diseases or conditions.

Neurofibromatosis and Osteoporosis

Compound I (PLX3397) prevented bone loss in neurofibromatosis affected mice by reducing osteoclast differentiation and bone resorptive activity in vivo (Yongzheng He et al., c-Fms Signaling Mediates Neurofibromatosis Type-1 Osteoclast Gain-In-Functions, PLOS ONE, November 2012, Volume 7, Issue 11, e46900). Thus, it is contemplated that Compound I can be a potential therapeutic agent for treating neurofibromatosis type 1 (NF1) associated osteoporosis and osteopenia.

Alzheimer's Disease

It was found that CSF1R inhibits microglial proliferation and prevents the progression of Alzheimer's-like pathology (Adrian Olmos-Alonso et al., Pharmacological targeting of CSF1R inhibits microglial proliferation and prevents the progression of Alzheimer's-like pathology, Brain., 2016: 139; 891-907).

Additionally, efficacy of CSF1R inhibition in models of Alzheimer's disease was demonstrated, and this validated the application of a therapeutic strategy aimed at modifying CSF1R activation as a promising approach to tackle microglial activation and the progression of Alzheimer's disease (Adrian Olmos-Alonso et al., Pharmacological Targeting of CSF1R Inhibits Microglial Proliferation and Prevents the Progression of Alzheimer's-like Pathology, Brain, March 2016, 139(3):891-907).

Progressive Supranuclear Palsy (PSP) and Alzheimer's Disease (AD)

It was reported that PSP and AD disease severity correlated with neuro-inflammation in the regions most closely associated with neuropathological changes characteristic of each disease, and data, together with previous genetic and epidemiological evidence, suggest that immunotherapeutic strategies could be useful in slowing the progression of neurodegenerative disorders like AD and PSP (L. Passamonti et al., [11C]PK11195 PET in Alzheimer's disease and progressive supranuclear palsy: The NIMROD Study, Poster Session, Jun. 28, 2017. See also Han et al. described herein for CSF1R inhibitors useful for treating neuroinflammation.

Epilepsy

The CSF1R blockade was validated in two pre-clinical models of epilepsy using a small molecule inhibitor of CSF1R, demonstrating that the CSF1R blockade can be a novel therapeutic strategy in epilepsy (Prashant K Srivastava et al., A systems-level framework for drug discovery identifies CSF1R as a novel anti-epileptic drug target, May 22, 2017, http://dx.doi.org/10.1101/140087.).

Brain Trauma

CSF1R inhibition by Compound I (PLX3397) effectively depleted microglia, and the depletion of microglia was sustained after intracerebral hemorrhage. It was further reported that the benefit of colony-stimulating factor 1 receptor inhibition by Compound I was associated with reduced leukocyte infiltration in the brain, and this confers protection after intracerebral hemorrhage (Minshu Li et el., Colony stimulating factor 1 receptor inhibition eliminates microglia and attenuates brain injury after intracerebral hemorrhage, Journal of Cerebral Blood Flow & Metabolism, 2017, Vol. 37(7) 2383-2395).

Tauopathies

It was reported that the importance of microglia in tau propagation is emphasized by the marked reduction of tau propagation by depletion of microglia by a CSF1R inhibition, which can be accomplished by Compound I (PLX3397) (Hirohide Asai et al., Depletion of microglia and inhibition of exosome synthesis halt tau propagation, Nature Neuroscience, November 2015, Vol. 18, 11).

Non-Small Cell Lung Cancer/Lung Cancer

CSF-1R functions as a tumor promoter in non-small-cell carcinoma (NSCLC) by regulation of the activity of Wnt family member 3a (Wnt3a) and accelerating epithelial-mesenchymal transition (EMT), migration, invasion and metastasis. Thus, the CSF-1R protein constitutes a promising therapeutic target to resolve tumor progression and dissemination (Yan Xia Yu et al., CSF-1R regulates non-small cell lung cancer cells dissemination through Wnt3a signaling, Am J Cancer Res., 2017, 7(11): 2144-2156).

Eye Diseases (Anterior and Posterior)

It was reported that microglia can be removed temporarily by a CSF1R inhibitor in order to reduce inflammation, and can be useful as a therapeutic intervention for degenerative or inflammatory disorders of the retina (Wai T. Wong, Science Daily, Mar. 21, 2018, https://www.sciencedaily.com/releases/2018/03/180321141403.htm).

Lysosomal Storage Diseases

Neuroinflammation in lysosomal storage diseases is typically elicited as a protective response following CNS injury, infection, or disease, and such inflammation can exert detrimental effects on neural cells. It was further reported that microglia are the principal neuroinflammatory cells in the CNS parenchyma cells (Megan E. Bosch et al., Neuroinflammatory paradigms in lysosomal storage diseases, Frontiers in Neuroscience, Oct. 30 2015, doi: 10.3389/fnins.2015.00417 (Page 2)).

Multiple Sclerosis

Blocking CSF1R can prevent immune cells from promoting the inflammation associated with multiple sclerosis (Andrea Morandi et al., The Colony-Stimulating Factor-1 (CSF-1) Receptor Sustains ERK1/2 Activation and Proliferation in Breast Cancer Cell Lines, Multiple Sclerosis News Today, Oct. 27, 2017, https://multiplesclerosisnewstoday.com/2017/10/27/mspans2017-study-shows-that-inhibiting-protein-in-brain-cells-canrejuvenate-myelin/).

Neuro-Inflammation and Neuroinflammatory Disorders

Microglia depletion and subsequent repopulation at defined stages holds promise for designing strategies to resolve neuroinflammation and promote recovery, and global depletion of microglia followed by repopulation can be accomplished with CSF1R inhibitors (Han et al., An updated assessment of microglia depletion: current concepts and future directions, Molecular Brain, (2017) 10:25 (See Abstract and page 3)).

Complex Regional Pain Syndrome

It was reported that neurogenic neuroinflammation may contribute to the multifactorial pathogenesis of complex regional pain syndrome (Littlejohn G., Neurogenic neuroinflammation in fibromyalgia and complex regional pain syndrome, Nat Rev Rheumatol, 2015 November; 11 (11):639-48). See also Han et al. described herein for CSF1R inhibitors useful for treating neuroinflammation.

Dementias

It was also reported that neuroinflammation has been increasingly implicated as a pathological mechanism in dementia, and demonstration that it is a key event accelerating cognitive or functional decline would inform novel therapeutic approaches (Stefaniak J et al., Imaging of neuroinflammation in dementia, J Neurol Neurosurg Psychiatry, 2016 January; 87(1):21-8). See also Han et al., above for CSF1R inhibitors useful for treating neuroinflammation.

HIV

Chronic microglial activation and associated neuroinflammation are key factors in neurodegenerative diseases, including HIV-associated neurocognitive disorders (Audrey C Knight et al., Increased Microglial CSF1R Expression in the SIV/Macaque Model of HIV CNS Disease, 8 Jan. 2018, Journal of Neuropathology & Experimental Neurology, Volume 77, Issue 3, 1 Mar. 2018, Pages 199-206, (See Abstract). See also Han et al. described herein for CSF1R inhibitors useful for depleting microglia.

Cerebral Palsy

It has been reported that there is evidence highlighting a central role for glia in mediating increased risk of disability in premature infants, including excessive activation of microglia (Carina Mallard et al., Astrocytes and microglia in acute cerebral injury underlying cerebral palsy associated with preterm birth, Pediatric Research, 2014, Vol. 75, 1 (See Abstract)) See also Han et al. described herein for CSF1R inhibitors useful for depleting microglia.

Glaucoma

There is clinical evidence for neuroinflammation in glaucoma and neuroinflammation, and neuroinflammation is defined as immune-relevant responses by cell types such as microglia glaucoma (Pete A Williams et al., Neuroinflammation in glaucoma: A new opportunity, Exp Eye Res. 2017 April, 157: 20-27 (See Abstract)). See also Han et al. above for CSF1R inhibitors useful for depleting microglia.

Bladder Cancer, Ovarian Cancer, Prostate Cancer, Pancreatic Cancer, and Colorectal Cancer It has been shown that CSF-1/CSF-1R was highly expressed in human tumor tissue, such as bladder cancer, ovarian cancer, prostate cancer, colorectal cancer, and pancreatic cancer (Li Huang et al., The possible mechanisms of tumor progression via, CSF-1/CSF-1R pathway activation, Rom J Morphol Embryol, 2014, 55(2 Suppl):501-506 (See page 502)).

Acute Myeloid Leukemia (AML) and Other Leukemias

It was shown that the expression of FLT3 was high in normal hemopoietic tissues and, in leukemia, FLT3 was specifically upregulated in AML and acute lymphocytic leukemia, indicating that a high expression of FLT3 may contribute to the progression of leukemia (Jie Cheng et al., High expression of FLT3 is a risk factor in leukemia, Molecular Medicine Reports, 2018, 17: 2885-2892 (See Discussion and FIG. 1)).

Breast Cancer

It was reported that the wide expression of the CSF-1/CSF-1R pair across breast cancer cell subtypes supports CSF-1/CSF-1R targeting in breast cancer therapy (Andrea Morandi et al., The Colony-Stimulating Factor-1 (CSF-1) Receptor Sustains ERK1/2 Activation and Proliferation in Breast Cancer Cell Lines, PLOS ONE, November 2011, Vol. 6, 11, e27450 (see Abstract)).

Cholangiocarcinoma

It was shown that that c-kit expression is detectable in biliary tract cancer (cholangiocarcinoma), and chimeric mice injected with c-kit positive human biliary tract cancer cells were treated with the c-kit inhibitor imatinib mesilate resulting in significantly reduced tumor volume and mass (Thomas Kamenz et al., Expression of c-kit receptor in human cholangiocarcinoma and in vivo treatment with imatinib mesilate in chimeric mice, World J Gastroenterol., 2006 Mar. 14; 12(10): 1583-1590 (see Page 1583)).

Endometrial Cancer

It was reported that there was a high level of expression of fms proto-oncogene mRNA in clinically aggressive human endometrial adenocarcinomas (Barry M. Kacinski et al., High level expression of fms proto-oncogene mRNA is observed in clinically aggressive human endometrial adenocarcinomas, International Journal of Radiation Oncology*Biology*Physics, November 2011, Vol. 6, 11, e27450)

Esophageal Cancer

It was shown that there were expressions of KIT in the small cell carcinoma component of the esophageal carcinoma (Tadashi Terada et al., Esophageal combined carcinomas: Immunohoistochemical and molecular genetic studies, World J Gastroenterol., 2012 Apr. 7, 18(13): 1545-1551 (See last sentence of Page 1549)).

Glioblastoma, Glioma

It was shown that CSF-1R inhibition blocks malignant progression and regresses established gliomas, and enhances survival in glioblastoma human xenografts (Stephanie M. Pyonteck et al., CSF-1R inhibition alters macrophage polarization and blocks glioma progression, Nat. Med., October 2013, 19(10):1264-1272).

Giant Cell Tumor

It was reported that administration of CSF1R inhibitor RG7155 to patients translated into clinical objective responses in diffuse-type giant cell tumor patients. (Carola H. Ries et al., Targeting Tumor-Associated Macrophages with Anti-CSF-1R Antibody Reveals a Strategy for Cancer Therapy, Cancer Cell, Jun. 16, 2014, 25:846-859).

Hepatocellular Carcinoma (HCC)

A HCC patient study found that peritumoral CSF-1R is associated with intrahepatic metastasis, tumor recurrence, and patient survival after hepatectomy, and CSF-1R may become a potential therapeutic target for postoperative adjuvant treatment (Jin-Bin Jia et al., High Expression of Macrophage Colony-Stimulating Factor-1 Receptor in Peritumoral Liver Tissue Is Associated with Poor Outcome in Hepatocellular Carcinoma After Curative Resection, The Oncologist 2010; 15:000-000)

Hodgkin Lymphoma

It was reported that administration of Compound I (PLX3397) to a heavily pretreated patient cohort affected by Hodgkin Lymphoma resulted in modest efficacy with a manageable safety profile and with evidence of target inhibition that may warrant further testing in combination therapy trials (Alastair J. King et al., CSF1R Inhibition by PLX3397 in Patients with Relapsed or Refractory Hodgkin Lymphoma: Results From a Phase 2 Single Agent Clinical Trial, Blood, 2012 120:1638 (See Discussion on Page 2)).

Melanoma

It was reported that Compound I (PLX3397) treatment of mouse melanoma models with tumor-specific CD8 T cells strongly promoted the control of tumor outgrowth (Sluijter M et al., Inhibition of CSF-1R Supports T-Cell Mediated Melanoma Therapy, PLOS ONE, 2014, 9(8) (See Page 1)).

Mesothelioma

Data were reported suggesting that CSF-1R signaling may have a critical pathogenic role in mesothelioma, and therefore may represent a promising target for therapeutic intervention (M Cioce et al., Autocrine CSF-1R signaling drives mesothelioma chemoresistance via AKT activation, Cell Death and Disease (2014) 5, e1167; doi:10.1038/cddis.2014.136 (See Page 1)).

Renal Cell Carcinoma (RCC)

It was reported that targeting CSF-1/CSF-1R signaling may be therapeutically effective in RCCs. (Julia Menke et al., Autocrine CSF-1 and CSF-1 Receptor Coexpression Promotes Renal Cell Carcinoma Growth, Cell Death and Disease (2014) 5, e1167; doi:10.1038/cddis.2014.136 (See Page 1)).

Malignant Peripheral Nerve Sheath Tumors (MPNST) and Plexiform Neurofibroma

Treatment of MPNST xenograft samples with Compound I (PLX3397) resulted in sustained blockade of c-Kit, c-Fms and PDGFRβ, resulting in significant suppression of tumor growth, and that data strongly suggested that PLX3397 is superior to imatinib in the treatment of MPNST (Parag P. Patwardhan et al., Sustained inhibition of receptor tyrosine kinases and macrophage depletion by PLX3397 and rapamycin as a potential new approach for the treatment of MPNSTs, Clin Cancer Res. 2014 Jun. 15; 20(12): 3146-3158 (See Page 1). Further, plexiform neurofibroma is a known precursor legion of MPNST (McCarron K F et al., Plexiform neurofibroma with and without associated malignant peripheral nerve sheath tumor: a clinicopathologic and immunohistochemical analysis of 54 cases, Mod Pathol. 1998 July; 11(7):612-7 (See Abstract)).

Salivary Gland Neoplasms

C-kit expression was observed through immunochemical staining in 4 different salivary gland neoplasms, and c-kit expression was found in both benign and malignant forms of salivary gland neoplasms (Salehinejad J et al., Evaluation of c-kit protein (CD117) expression in common salivary gland neoplasms, J Oral Maxillofac Pathol., 2014 May; 18(2):177-82 (See Abstract)).

Gastrointestinal Stromal Tumor

It was reported that c-kit is the crucial step in tumorigenesis of gastrointestinal stromal tumors (GIST), and the c-kit inhibitor imatinib can block the activated receptor tyrosine kinase activity of c-kit to result in objective responses in advanced GIST patients (Siehl J et al., C-kit, GIST, and imatinib, Recent Results Cancer Res. 2007; 176:145-51 (See Abstract)).

Pigmented Villonodular Synovitis (PVNS) and Tenosynovial giant cell tumor (TGCT)

It was reported that Compound I met its primary endpoint in phase III clinical trials for the treatment of TGCT, wherein the primary endpoint was tumor response measured by tumor size reduction. TGCT is a group of cancers that include pigmented villonodular synovitis (PVNS) and giant cell tumors of the tendon sheath (GCT-TS) (Mark Terry, Daiichi Sankyo's Tumor Drug Meets Primary Endpoint in Late-Stage Study, Oct. 31, 2017, https://www.biospace.com/article/daiichi-sankyos-tumor-drug-meets-primary-endpoint-in-late-stage-study/).

Catatonia, Schizophrenia

Janova et al. demonstrated that the administration of a CSF1R inhibitor alleviated catatonic symptoms in mice in a phenotyped schizophrenic sample (Janova et al., Microglia ablation alleviates myelin-associated catatonic signs in mice, Clin Invest. 2018; 128(2):734-745 (See Abstract)).

Brain Calcification

Daida et al. reported that patients with CSF1R mutations and brain calcification were detected on CT scans. (Daida et al., CSF1R Mutation p.G589R and the Distribution Pattern of Brain Calcification, *Intern Med,* 56: 2507-2512, 2017).

Retinitis Pigmentosa

Blank et al. stated that inhibiting microglial activation can provide useful approaches to prevent retinal degeneration in retinitis pigmentosa (Blank et al., Early Microglia Activation Precedes Photoreceptor Degeneration in a Mouse Model of CNGB1-Linked Retinitis Pigmentosa, *Front. Immunol.,* 5 Jan. 2018 (See Conclusion on page 9)).

Retinal Microglial Homeostasis

Zhang et al. found that there was complete homeostatic recovery of microglial organization in the retina following microglial ablation using a CSF1R inhibitor in one of the studies (Zhang et al., Repopulating retinal microglia restore endogenous organization and function under CX3CL1-CX3CR1 regulation, *Science Advances,* 21 Mar. 2018).

Chronic Traumatic Encephalopathy (CTE)

CTE has been defined as a progressive degenerative disease, which afflicts the brain of people who have suffered repeated concussions and traumatic brain injuries, and microglia drives the continuous low-level inflammation associated with the insidious onset of CTE (Donal et al., Microglial Activation in Traumatic Brain Injury, *Frontiers in Ageing Neuroscience*, June 2017, Volume 9, Article 208 Frontiers in Ageing Neuroscience). Minshu Li et el., described above reported that CSF1R inhibition eliminates microglia and attenuates brain injury.

Provided herein are methods for treating a subject suffering from or at risk of a disease or condition mediated by a protein kinase selected from c-fms, c-kit, Flt3 or combinations thereof and/or macrophages or microglia, comprising administering to the subject a therapeutically effective amount of a composition described herein.

In some embodiments, the diseases treatable with any of the compositions of this disclosure are c-Fms mediated disease selected from the group consisting of immune disorders, including, but not limiting to, rheumatoid arthritis, systemic lupus erythematosis (SLE), and transplant rejection; stem cell ablation and myelopreparation for stem cell transplant; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), pen-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), monocytic leukemia, prostate cancer, breast cancer, ovarian cancer, melanoma, glioblastoma multiforme, tauopathies, metastasis of tumors to other tissues, and other chronic myeloproliferative diseases such as myelofibrosis. In some embodiments, the AML is associated with Fms-like tyrosine kinase 3 (Flt3) mutations that are internal tandem duplication (ITD) mutations. In some embodiments, the c-Fms mediated diseases include tumors that express aberrantly or otherwise Fms, CSF1R, CSF1 or IL-34, or activating mutations or translocations of any of the foregoing.

In other embodiments, the disease or condition is mediated by c-Fms and c-Kit and is selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia, malignant peripheral nerve cell tumors, malignant peripheral nerve sheath tumors, pheochromocytomas cutaneous and plexiform neurofibromas, neurofibromatosis, neurofibromatosis-1 (NF1), leiomyo-adenomatoid tumor, leiomyo sarcoma, acute myeloid leukemia, acute lymphocytic leukemia, chronic myelogenous leukemia, multiple myeloma, mastocytosis, melanoma, breast cancer, ovarian cancer, prostate cancer, canine mast cell tumors, metastasis of cancer to bone or other tissues, chronic myeloproliferative diseases such as myelofibrosis, renal hypertrophy, asthma, rheumatoid arthritis, allergic rhinitis, multiple sclerosis, osteoarthritis, inflammatory bowel syndrome, transplant rejection, systemic lupus erythematosis, ulcerative colitis, Crohn's disease, chronic obstructive pulmonary disease, emphysema, Kawasaki's Disease, hemophagocytic syndrome (macrophage activation syndrome), multicentric reticulohistiocytosis, atherosclerosis, Type I diabetes, Type II diabetes, insulin resistance, hyperglycemia, obesity, lipolysis, hypereosinophilia, osteoporosis, increased risk of fracture, Paget's disease, hypercalcemia, infection-mediated osteolysis (e.g. osteomyelitis), peri-prosthetic or wear-debris-mediated osteolysis, endometriosis, glomerulonephritis, interstitial nephritis, Lupus nephritis, tubular necrosis, diabetic nephropathy, stroke, Alzheimer's disease, Parkinson's disease, inflammatory pain, chronic pain, and bone pain.

In some embodiments, the disease or condition (mediated by a protein kinase selected from c-fms, c-kit, Flt3 or combinations thereof and/or macrophages or microglia) treatable with any of the compositions of this disclosure is selected from alopecia, baldness, wound healing, androgenetic alopecia (AGA), epilepsy, traumatic brain injury, tauopathies, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodies, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, frontotemporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST—which includes, without limitation, $1^{st}$ line, $2^{nd}$ line and neoadjuvant GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth; and tumors that express aberrantly or otherwise Fms, CSF1R, CSF1 or IL-34, or activating mutations or translocations of any of the foregoing.

In some embodiments, the disease or condition (mediated by a protein kinase selected from c-fms, c-kit, Flt3 or combinations thereof and/or macrophages or microglia) treatable with any of the compositions of this disclosure is selected from alopecia, baldness, wound healing, androgenetic alopecia (AGA), epilepsy, traumatic brain injury, tauopathies, Alzheimer's Disease, schizophrenia, catatonia, chronic traumatic encephalopathy, cardiac inflammation, retinitis pigmentosa, brain calcification, Erdheim Chester Disease, Langerhans cell histocytosis, hairy cell leukemia, non-small cell lung cancer, cleroderma, anterior eye disease, posterior eye disease, lysosomal storage disease, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodies, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, ureter cancer, urethra cancer, urachus cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, angiosarcomas, liposarcomas, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), tumor angiogenesis, paracrine tumor growth or tumors that express aberrantly or otherwise Fms, CSF1R, CSF1 or IL-34, or activating mutations or translocations of any of the foregoing.

In some embodiments, the disease or condition mediated by a protein kinase selected from c-fms, c-kit, Flt3 or combinations thereof and/or macrophages or microglia treatable with any of the compositions of this disclosure is selected from osteoporosis, neurofibromatosis, Alzheimer's disease, epilepsy, traumatic brain injury, tauopathies, non-small cell lung cancer, anterior eye disease, posterior eye disease, lysosomal storage disease, multiple sclerosis, complex regional pain syndrome, neuro-inflammation, neuroinflammatory disorders, HIV, binswager type dementia, dementia with lewy bodies, cerebral palsy, progressive supranuclear palsy, glaucoma, vascular dementias, multi infarct dementia, fronto temporal dementia, pseudo-dementia, bladder cancer, acute myeloid leukemia, chronic lymphocytic leukemia, breast cancer, cholangiocarcinoma, colon cancer, endometrial cancer, esophageal cancer, glioma, glioblastoma, hepatocellular carcinoma, Hodgkin lymphoma, leukemia, lung cancer, melanoma, mesothelioma, pancreatic cancer, renal cancer, monocytic leukemia, malignant peripheral nerve sheath tumors (MPNST), plexiform neurofibromas, salivary gland tumors, mucoepidermoid carcinoma of the salivary gland, acinic cell carcinoma of the salivary gland, gastrointestinal stromal tumors (GIST), giant cell tumors (GCT), GCT of bone, pigmented villonodular synovitis (PVNS), tenosynovial giant cell tumor (TGCT), TCGT of tendon sheath (TGCT-TS), schizophrenia, catatonia, chronic traumatic encephalopathy, cardiac inflammation, retinitis pigmentosa, or brain calcification, or diseases or conditions that express aberrantly or otherwise Fms, CSF1R, CSF1 or IL-34, or activating mutations or translocations of any of the foregoing.

In some embodiments, the disease or condition treatable with any of the compositions of this disclosure is selected from melanoma, primary progressive multiple sclerosis, malignant peripheral nerve sheath tumors (MPNST), plexiform neurofibromas, mesothelioma, multi infarct dementia, fronto temporal dementia, mucoepidermoid carcinoma of the salivary gland, gastrointestinal stromal tumors (GIST—which includes, without limitation, $1^{st}$ line, $2^{nd}$ line and neoadjuvant GIST), pigmented villonodular synovitis (PVNS) or tenosynovial giant cell tumor (TGCT).

In some embodiments, the disclosure provides a method for treating a subject suffering from or at risk of tenosynovial giant cell tumor (TGCT) comprising administering to the subject a therapeutically effective amount of any of the compositions of this disclosure. In some embodiments, the disclosure provides a method for treating a subject suffering from or at risk of pigmented villonodular synovitis (PVNS) comprising administering to the subject a therapeutically effective amount any of the compositions of this disclosure. In some embodiments, the disclosure provides a method for treating a subject suffering from or at risk of malignant peripheral nerve sheath tumors (MPNST) comprising administering to the subject a therapeutically effective amount of any of the compositions of this disclosure. In some embodiments, the disclosure provides a method for treating a subject suffering from or at risk of plexiform neurofibromas comprising administering to the subject a therapeutically effective amount of any of the compositions of this disclosure. In some embodiments, the disclosure provides a method for treating a subject suffering from or at risk of malignant peripheral nerve sheath tumors (MPNST) comprising administering to the subject a therapeutically effective amount any of the compositions of this disclosure.

In other embodiments, the disclosure provides methods for treating a Fms-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity (e.g. kinase activity). In some embodiments, the methods may involve administering to the subject suffering from or at risk of a Fms-mediated disease or condition a therapeutically effective amount of any of the compositions of this disclosure. In one embodiment, the Fms mediated disease is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and penprosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, a subset of glioblastoma, proneural subset of glioblastoma, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, CLN-6 Batten Disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); surgical indications, including but not limited to (cardiopulmonary) bypass surgery, vascular surgery, and vascular grafts; and tumors that express aberrantly or otherwise Fms, CSF1R, CSF1 or IL-34, or activating mutations or translocations of any of the foregoing.

In another embodiment of this disclosure, the CSF1R (Fms) mediated disease that can be treated by any of compositions in this disclosure is epilepsy.

In another embodiment of this disclosure, the CSF1R (Fms) mediated disease that can be treated by any of compositions in this disclosure is traumatic brain injury.

In another embodiment of this disclosure, the CSF1R (Fms) mediated disease that can be treated by any of compositions in this disclosure, in combination with dovitinib or vatalanib, is glioblastoma (GBM).

In another embodiment of this disclosure, the CSF1R (Fms) mediated disease that can be treated by any of compositions in this disclosure include tauopathies.

In another embodiment of this disclosure, the CSF1R (Fms) mediated disease that can be treated by any of compositions in this disclosure include reducing viral reservoirs in patients.

In another embodiment of this disclosure, the CSF1R (Fms) mediated disease that can be treated by any of compositions in this disclosure include Erdheim Chester Disease/Langerhans cell histiocytosis, hairy cell leukemia, and non-small cell lung cancer (NSCLC).

In another embodiment of this disclosure, a disease that can be treated by any of compositions in this disclosure is scleroderma. In this embodiment, a composition of this disclosure is administered topically, and can be administered in a topical formulation such as a gel, cream or spray as non-limiting examples.

In another embodiment of this disclosure, the CSF1R (Fms) mediated disease that can be treated by any of compositions in this disclosure is anterior eye disease or posterior eye disease. Examples of these eye diseases include diseases of the cornea, conjunctiva, sclera, and lacrimal glands. In some embodiments, a composition of this disclosure is a formulation suitable for administration to the eye, including, but not limited to, eye drops.

In aspects and embodiments involving treatment of a disease or condition with any of the compositions of this disclosure, the disclosure provides methods for treating a disease or condition mediated by Fms and Kit in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and Kit activity (e.g. kinase activity).

In some embodiments, the methods may involve administering to the subject suffering from or at risk of a disease or condition mediated by Fms and Kit an effective amount of one or more composition(s) as described herein. In one embodiment, the condition mediated by Fms and Kit is selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosus, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, neurofibromatosis (including Schwann cell neoplasia associated with neurofibromatosis), mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary arterial hypertension.

Combinations

In some embodiments, the disclosure provides a method of treating a subject suffering from a disease or condition described in this disclosure, said method comprising administering to the subject an effective amount of any of the compositions of this disclosure, in combination with immunotherapy such as i) a PD-L1 inhibitor (such as durvalumab, nivolumab, panitumumab, pertuzumab, rituximab, tositumomab, trastuzumab, and 90 Y ibritumomab tiuxetan, ii) a PD-1 inhibitor such as pembrolizumab iii) an IDO inhibitor (such as indoximod), iv) a monoclonal antibody such as ranibizumab or bevacizumab, or v) a kinase inhibitor, including, but not limited to FLT3 inhibitors such as quizartinib. In some embodiments, the method of treating a subject suffering from a disease or condition described in this disclosure comprises administering to the subject an effective amount of any of the compositions of this disclosure in combination a therapeutically effective amount of an IDO inhibitor (such as indoximod) for treating an infectious disease. Non-limiting examples of infectious diseases include a viral infections such as influenza, hepatitis C virus (HCV), human papilloma virus (HPV), cytomegalovirus (CMV), Epstein-Barr virus (EBV), poliovirus, varicella zoster virus, coxsackie virus, and human immunodeficiency virus (HIV). In some embodiments, the method of treating a subject suffering from a disease or condition described in this disclosure comprises administering to the subject an effective amount of any of the compositions of this disclosure in combination a therapeutically effecitive amount of PD-L1 inhibitor (such as durvalumab, nivolumab, panitumumab, pertuzumab, rituximab, tositumomab, trastuzumab, and 90 Y ibritumomab tiuxetan, for treating a c-Kit or c-Fms related disease as described in this disclosure. Another embodiment of this disclosure provides a method of treating a subject suffering from a disease or condition described in this disclosure, said method further comprising administering to the subject a PD-L1 inhibitor, a PD-1 inhibitor, an IDO inhibitor, a monoclonal antibody, or a FLT3 kinase inhibitor.

Compound I can deplete microglia, which can inhibit tau propogation. Exosome inhibitors halt tau propagation. In some embodiments, the method of treating a subject suffering from a disease or condition described in this disclosure comprises administering to the subject a therapeutically effective amount of any of the compositions of this disclosure, in combination with a therapeutically effeicitive amount of an exosome inhibitor, wherein the disease or condition is modulated by Tau propagation. Non-limiting examples of diseases or conditions that are modulated by Tau propagation include Alzheimers disease, Parkinson's disease and dementia.

In some embodiments, the disclosure provides a method of treating a subject suffering from a disease or condition described in this disclosure, said method comprising administering to the subject a therapeutically effective amount of any of the compositions of this disclosure in combination with a c-Kit protein kinase inhibitor or mutant c-Kit protein kinase inhibitor. In another embodiment, the mutant c-Kit protein kinase inhibitor is selected from (2-phenyl-1H-pyrrolo[2,3-b]pyridin-5-yl)-(3-pyridyl)methanol, (2-phenyl-1H-pyrrolo[2,3-b]pyridin-5-yl)-(3-pyridyl)methanone, N-(3-carbamoylphenyl)-2-phenyl-1H-pyrrolo[2,3-b]pyridine-5-carboxamide, 2-phenyl-N-(1H-pyrazol-3-yl)-1H-pyrrolo[2,3-b]pyridine-5-carboxamide, 4-bromo-N-(2-phenyl-1H-pyrrolo[2,3-b]pyridin-5-yl)-1H-pyrazole-5-carboxamide, ethyl 3-[(2-phenyl-1H-pyrrolo[2,3-b]pyridin-5-yl)carbamoylamino]propanoate, 3,4-dimethyl-N-(2-phenyl-1H-pyrrolo[2,3-b]pyridin-5-yl)-1H-pyrazole-5-carboxamide, 4-methyl-3-phenyl-N-(2-phenyl-1H-pyrrolo[2,3-b]pyridin-5-yl)-1H-pyrazole-5-carboxamide, 3-cyclopropyl-N-(2-phenyl-1H-pyrrolo[2,3-b]pyridin-5-yl)-1H-pyrazole-5-carboxamide, 5-fluoro-N-(2-phenyl-1H-pyrrolo[2,3-b]pyridin-5-yl)-1H-indazole-3-carboxamide, N-(2-phenyl-1H-pyrrolo[2,3-b]pyridin-5-yl)pyrimidine-4-carboxamide, 3-fluoro-N-(2-phenyl-1H-pyrrolo[2,3-b]pyridin-5-yl)pyridine-2-carboxamide, 3,5-dimethyl-N-(2-phenyl-1H-pyrrolo[2,3-b]pyridin-5-yl)isoxazole-4-carboxamide, N-(2-phenyl-1H-pyrrolo[2,3-b]pyridin-5-yl)pyridazine-3-carboxamide, N-(2-phenyl-1H-pyrrolo[2,3-b]pyridin-5-yl)-2H-triazole-4-carboxamide, 3-methyl-N-(2-phenyl-1H-pyrrolo[2,3-b]pyridin-5-yl)pyridine-2-carboxamide, 4,5-dimethyl-N-(2-phenyl-1H-pyrrolo[2,3-b]pyridin-5-yl)isoxazole-3-carboxamide or N-(2-phenyl-1H-pyrrolo[2,3-b]pyridin-5-yl)-1H-pyrazole-4-sulfonamide.

In another embodiment, Compound I Form C is combined with any of the mutant c-Kit mutant inhibitors described in this disclosure for treating GIST—which includes, without limitation, $1^{st}$ line, $2^{nd}$ line and neo-adjuvant GIST.

In some embodiments, the disclosure provides a method of treating a cancer in a subject in need thereof by administering to the subject an effective amount of a composition of this disclosure in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. X-ray, γ-ray, or electron, proton, neutron, or cc particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e g aminolevulinic acid, motexafin lutetium), oncolytic viral or bacterial therapy, surgery, or bone marrow and stem cell transplantation. In certain embodiments, the disclosure provides a method of treating a cancer in a subject in need thereof by administering to the subject an effective amount of a composition as described herein and applying a radiation treatment as described herein either separately or simultaneously. In one embodiment, the disclosure provides a method for treating a cancer in a subject in need thereof by administering an effective amount of a composition as described herein to the subject followed by a radiation treatment (e.g. X-ray, γ-ray, or electron, proton, neutron, or cc particle beam). In another embodiment, the disclosure provides a method for treating a cancer in a subject in need thereof by applying a radiation treatment (e.g. X-ray, γ-ray, or electron, proton, neutron, or cc particle beam) to the subject followed by administering an effective amount of a composition as described herein to the subject. In yet another embodiment, the disclosure provides a method for treating a cancer in a subject in need thereof by administering a composition as described herein and a radiation therapy (e.g. X-ray, γ-ray, or electron, proton, neutron, or α particle beam) to the subject simultaneously.

In some embodiments, the disclosure provides a method for treating a melanoma or a metastatic melanoma with a KIT mutation in a subject comprising administering to the subject a therapeutically effective amount any of the compositions in this disclosure.

In some embodiments, the method of treating a subject suffering from or at risk of melanoma with any of the compositions of this disclosure further comprises administering to the subject a therapeutically effective amount of pembrolizumab.

Kinase Activity Assays

A number of different assays for kinase activity can be utilized for assaying for active modulators and/or determining specificity of a modulator for a particular kinase or group of kinases, such as those described in U.S. Pat. Pub. No. 2014/0037617, which is hereby incorporated by reference in its entirety. One of ordinary skill in the art can readily identify other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Definitions

As used herein the following definitions apply unless clearly indicated otherwise.

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

The term "crystalline form" refers to polymorphs as well as solvates, hydrates, etc. The term "polymorph" refers to a particular crystal structure having particular physical properties such as X-ray diffraction, melting point, and the like. "Crystalline form" means that greater than 50%; or greater than 55%; or greater than 60%; or greater than 65%; or greater than 70%; or greater than 75%; or greater than 80%; or greater than 85%; or greater than 90%; or greater than 95% of the compound present in a composition is in crystalline form.

As used herein, the terms "treat," "treating," "therapy," "therapies," and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

Compound I (also known as PLX3397 or pexidartinib) is an inhibitor of Fms, Kit and Flt3 protein kinases. The kinase assays that can measure the $IC_{50}$ values for these targets are described in US Publication Nos. US 2007/0032519, US 2009/0076046 and US 2011/0112127. Compound I has $IC_{50}$ values of less than 0.05 μM for each of these three kinase targets.

As used herein, the term "Fms and/or Kit and/or Flt3 protein kinase mediated disease or condition" refers to a disease or condition in which the biological function of a Fms protein kinase, including any mutation thereof, a Kit protein kinase, including any mutation thereof, a Flt3 protein kinase, including any mutation thereof or both a Fms and Kit protein kinase, including any mutations thereof, affects the development, course, and/or symptoms of the disease or condition, and/or in which modulation of the Fms and/or Kit and/r Flt3 protein kinase alters the development, course, and/or symptoms of the disease or condition. A Fms and/or Kit and/or Flt3 protein kinase mediated disease or condition includes a disease or condition for which modulation provides a therapeutic benefit, e.g. wherein treatment with Fms and/or Kit and/or Flt3 protein kinase inhibitor(s), including any of the compositions described in this disclosure, and optionally in combination with another therapeutic agent or therapy as described herein provides a therapeutic benefit to the subject suffering from or at risk of the disease or condition.

As used herein, the terms "Fms protein kinase mediated disease or condition," "c-Fms mediated disease or condition," and the like refer to a disease or condition in which the biological function of a Fms protein kinase, including any mutations thereof, affects the development, course, and/or symptoms of the disease or condition, and/or in which modulation of the Fms protein kinase alters the development, course, and/or symptoms of the disease or condition. The Fms protein kinase mediated disease or condition includes a disease or condition for which Fms inhibition provides a therapeutic benefit, e.g. wherein treatment with Fms inhibitor(s), including any of the composition of this disclosure, and optionally in combination with another therapeutic agent or therapy as described herein provides a therapeutic benefit to the subject suffering from or at risk of the disease or condition.

As used herein, the terms "Kit protein kinase mediated disease or condition," "c-Kit mediated disease or condition," and the like refer to a disease or condition in which the biological function of a Kit protein kinase, including any mutations thereof, affects the development, course, and/or symptoms of the disease or condition, and/or in which modulation of the Kit protein kinase alters the development, course, and/or symptoms of the disease or condition. The Kit protein kinase mediated disease or condition includes a disease or condition for which Kit inhibition provides a therapeutic benefit, e.g. wherein treatment with Kit inhibitor(s), including any of the compositions of this disclosure, and optionally in combination with another therapeutic agent or therapy as described herein provides a therapeutic benefit to the subject suffering from or at risk of the disease or condition.

As used herein, the term "composition" (also referred to herein as pharmaceutical composition) refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable solubilizing agent or excipient.

As used herein, the term "capsule formulation" refers to a capsule of any of the compositions in this disclosure. Non-limiting examples of capsule formulations include Formulation AA, Formulation AB, Formulation AC, Formulation AD, Formulation AE, and Formulation AF as described in this disclosure.

As used herein, the term "tablet formulation" refers to a tablet of any of the compositions in this disclosure. Non-limiting examples of capsule formulations include Formulation AA, Formulation AB, Formulation AC, Formulation AD, Formulation AE, and Formulation AF as described in this disclosure.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "about" used in the context of quantitative measurements means the indicated amount ±10%. For example, "about 2:8" would mean 1.8-2.2: 7.2-8.8. In some embodiments, the term "about" refers to ±5%, ±4%, ±3%, ±2%, or ±1%.

As used herein in the context of a pharmaceutically or biologically active compound (for example Compound I), the term "stable" refers to the ability of the compound to retain its activity or to retain certain physical or chemical properties under certain specified conditions. In some embodiments, an active compound is "stable" if the activity at the end of the specified period is at least 50%; or at least 60%; or at least 70%; or at least 75%; or at least 80%; or at least 85%; or at least 90%; or at least 95%; or at least 98% of the activity of the compound at the beginning of the specified period. In some embodiments, a compound in an crystalline form is stable if at least 50%; or at least 60%; or at least 70%; or at least 75%; or at least 80%; or at least 85%; or at least 90%; or at least 95%; or at least 98% of the compound remains in the crystalline form at the end of the specified period. In further embodiments, an crystalline compound is stable if it forms detectable crystalline peaks in XRPD profiles during the indicated period.

As used herein, the phrase "substantially as shown in Figure" as applied to DSC thermograms is meant to include a variation of ±3° Celsius and as applied to thermogravimetric analysis (TGA) is meant to include a variation off 2% in weight loss.

As used herein, the phrase "major peaks" in the XRPD pattern refers to a subset of the entire observed peak list. Major peaks are selected from observed peaks by identifying preferably non-overlapping, low-angle peaks, with strong intensity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "substantially crystalline" material embraces material which has greater than about 80% crystallinity In another embodiment, substantially crystalline" material embraces material which has greater than about 90% crystallinity In another embodiment, substantially crystalline embraces material which has greater than about 98% crystallinity The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. In certain embodiments, a "therapeutically-effective amount" of Compound I refers to such dosages and/or administration for such periods of time necessary to inhibit CSF1R and c-Kit. Moreover, a therapeutically effective amount may be one in which the overall therapeutically-beneficial effects outweigh the toxic or undesirable side effects. A therapeutically-effective amount of Compound I may vary according to disease state, age and weight of the subject being treated. Thus, dosage regimens are typically adjusted to the individual requirements in each particular case and are within the skill in the art. In certain embodiments, an appropriate daily dose for administration of Compound I to an adult human may be from about 100 mg to about 3200 mg; or from about 250 mg to about 2000 mg, although the upper limit may be exceeded when indicated. A daily dosage of Compound I can be administered as a single dose, in divided doses, or, for parenteral administration, it may be given as subcutaneous injection.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

As used herein, the term "mix" or "blend" is interchangeable and means to combine two or substances.

Abbreviations as used herein have respective meanings as follows:

| | |
|---|---|
| D | Days |
| DMSO | Dimethylsulfoxide |
| DSC | differential scanning calorimetry |
| DVS | dynamic vapor sorption |
| EtOAc | ethyl acetate |

| | |
|---|---|
| EtOH | Ethanol |
| HPLC | High pressure liquid chromatography |
| IPA | Isopropanol |
| IR | Infrared spectrum |
| kV | Kilovolt |
| mA | Milliampere |
| MeOH | Methanol |
| Pks | Peaks |
| RH | relative humidity |
| RT | room temperature |
| TGA | thermogravimetric analysis |
| μL | Microliter |
| μm | Micrometer |
| μM | Micromolar |
| v/v | volume to volume |
| W/W | Weight to Weight |
| XRPD | X-ray powder diffraction |

EXAMPLES

Examples related to the present disclosure are described below. In most cases, alternative techniques can be used. The examples are intended to be illustrative and are not limiting or restrictive to the scope of the disclosure.

Example 1: Compound I

Compound I was synthesized according to the following synthetic procedure:

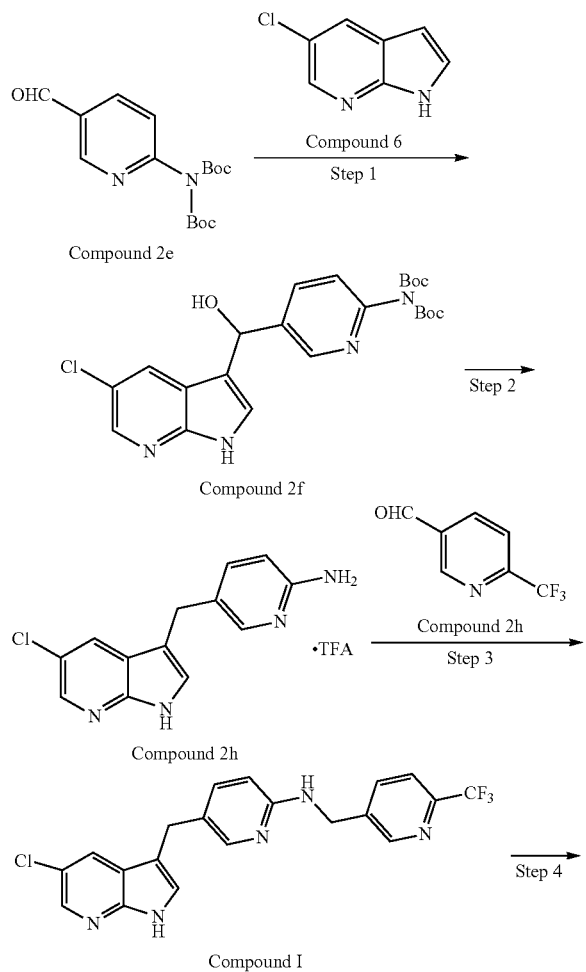
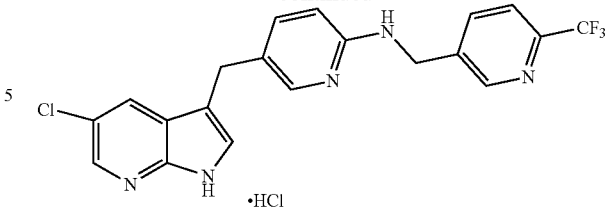

Step 1: Conversion of Compound 2e to Compound 2f

Commercially available di-tert-butyl (5-formylpyridin-2-yl)imidodicarbonate (Compound 2e), commercially available 5-chloro-1H-pyrrolo[2,3-b]pyridine) (Compound 6), (5-Chloro-1H-pyrrolo[2,3-b]pyridine), tetrabutylammonium bisulfate, and anhydrous isopropyl alcohol were added to a dry reactor blanketed with nitrogen. The reaction mixture was cooled to a temperature of 10 to 20° C. for about 3 hours with stirring, or until the solids were dissolved. Potassium tert-pentoxide, 25% in toluene, was added while maintaining an internal temperature of 10 to 20° C. The reaction mixture was stirred at 20 to 25° C. for a minimum of 20 hours. The reaction progress was monitored by analyzing the reaction mixture by HPLC. When compound 2f was no less than 80.0%, the reaction mixture is cooled to an internal temperature of −5 to 5° C. for a minimum of 2 hours. The solids were isolated by filtration, washed with cooled isopropyl alcohol, then dried under vacuum for a minimum of 12 hours until the residual isopropyl alcohol level was less than or equal to 12% w/w.

Step 2: Conversion of Compound 2f to Compound 2h

Compound 2f and acetonitrile under nitrogen were charged to a dry reactor blanketed with nitrogen and the resulting mixture was cooled to 0 to 10° C. with stirring. Triethylsilane and trifluoroacetic acid were added sequentially while maintaining an internal temperature of 0 to 10° C., and the reaction mixture was slowly heated to 55 to 65° C. and maintained at this temperature for about 20 hours. The reaction progress was monitored by analyzing the reaction mixture by HPLC. The product is precipitated by concentrating the volume, adding purified water, and concentrating again. The suspension was stirred for 1 to 3 hours at 45 to 60° C., cooled to 0 to 10° C., filtered, and the resulting solids were washed with purified water. The solids were then washed with n-heptane and dried under vacuum for about 12 hours to give Compound 2h.

Step 3: Conversion of Compound 2h to Compound I

Compound 2h, commercially available Compound F, and acetonitrile were charged to a dry reactor blanketed with nitrogen and the resulting mixture was stirred at a temperature of about 30° C. Trifluoroacetic acid and triethylsilane were added sequentially while maintaining temperature of less than or equal to 30° C., and the reaction mixture was heated to reflux and maintained at this temperature for about 24 hours. The reaction progress was monitored by analyzing the reaction mixture by HPLC. The reaction mixture was worked up by concentrating the volume, adding purified water, and concentrating again. Ethyl acetate was then added, followed by 25% sodium hydroxide solution to raise the pH of the mixture between 8 and 10. The lower aqueous layer was discarded and the upper organic layer was washed with purified water. The product was precipitated by concentrating the volume and adding n-heptane, and the resulting solids were filtered and washed with n-heptane. Ethyl acetate and purified water were added to the solids and the mixture was stirred with heating until completely dissolved.

Compound I was crystallized by concentrating the volume and adding n-heptane. The solids are filtered, washed with n-heptane, and dried under vacuum for a minimum of 12 hours until the weight loss is not more than 1%.

Step 4: Conversion of Compound I (Free Base) to Compound I (HCl Salt)

Compound I (free base) and methanol were charged to a dry reactor blanketed with nitrogen and the resulting mixture was stirred. Concentrated hydrochloric acid was added while maintaining a temperature of less than 30° C., and the mixture was stirred at 20 to 30° C. until a clear solution was observed. The solution was filtered through an in-line filter followed by a methanol rinse. Purified water was added to the solution while maintaining a temperature between 28 to 32° C. Seed crystals were added and the mixture was stirred for 1 to 3 hours at 28 to 32° C. Purified water was added to the resultant suspension while maintaining a temperature of 25 to 32° C. The mixture was then cooled to 0 to 7° C. for about 2 hours. The resultant solids were isolated by filtration and washed with a chilled methanol and methyl tert-butyl ether mixture, followed by a chilled methyl tert-butyl ether rinse. The solids were then re-suspended in a mixture of methyl tert-butyl ether and purified water, heated to reflux with stirring for about 6 hours, and the solids were isolated by filtration, washed with methyl tert-butyl ether, and dried under vacuum for a minimum of 12 hours. The dried solids were then sieved using a screening mill to break up large lumps to afford desired product (HCl salt of Compound I).

Example 2: Polymorphic Form C

Four crystalline forms were identified for the HCl salt of Compound I: Form A (unsolvated), Form B (hydrated mixture), Form C (unsolvated), and Form D (methanol solvate). Of these forms, Form C was most frequently observed and was the most physically stable form. Form C is a substantially crystalline form.

Compound I Form C was prepared by recrystallizing Compound I Form A from a solvent selected from acetone, 1,4-dioxane, ethanol, methanol, and a mixture of isopropanol and water. In another embodiment, Compound I Form C is prepared by recrystallizing Compound I Form A from ethanol. Compound I Form A is prepared by recrystallizing the HCl salt of Compound I from a mixture of methanol and water.

Compound I Form C is characterized by an X-ray powder diffractogram comprising peaks) (±0.2°) at 7.3, 23.3 and 28.2°2θ, as determined on a diffractometer using Cu-Kα radiation. The diffractogram comprises additional peaks (±0.2°) at 16.6 and 20.9°2θ. Form C is also characterized by its full X-ray powder diffractogram as substantially shown in FIG. 1. Major peaks in the XRPD pattern are shown in Table 1 below. In one embodiment, this disclosure provides Compound I Form C comprising two or more peaks (±0.2°) listed in the Table 1 below as determined on a diffractometer using Cu-Kα radiation.

XRPD data was collected using PANalytical X'Pert Pro Diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop was used to minimize the background generated by air scattering. Soller slits were used for the incident and diffracted beams to minimize axial divergence. Diffraction patterns were collected using a scanning position-sensitive detector (X'Celerator) located 240 mm from the specimen. Prior to the analysis a silicon specimen (NIST SRM 640c) was analyzed to verify the position of the silicon 111 peak.

TABLE 1

Major Peaks in the XRPD Pattern for Compound I Form C

| °2θ (±0.2°) | d-space [Å] |
|---|---|
| 7.3 | 12.176 ± 0.335 |
| 8.5 | 10.422 ± 0.245 |
| 13.8 | 6.427 ± 0.093 |
| 14.4 | 6.127 ± 0.084 |
| 15.2 | 5.820 ± 0.076 |
| 16.6 | 5.321 ± 0.063 |
| 16.9 | 5.240 ± 0.062 |
| 20.3 | 4.372 ± 0.043 |
| 20.9 | 4.239 ± 0.040 |
| 21.3 | 4.159 ± 0.039 |
| 22.4 | 3.968 ± 0.035 |
| 23.3 | 3.816 ± 0.032 |
| 26.7 | 3.331 ± 0.024 |
| 28.2 | 3.160 ± 0.022 |

In some embodiments, Form C is also characterized by its differential scanning calorimetry (DSC) curve comprising an endotherm comprising signal maximum at about 234° C. with an onset temperature of about 227° C. In another embodiment, the DSC curve is substantially as shown in FIG. 2.

In some embodiments, Form C is also characterized by thermogravimetric analysis (TGA) comprising a thermogram substantially as shown in FIG. 3.

In some embodiments, Form C is also characterized by a dynamic vapor sorption (DVS) curve substantially as shown in FIG. 4.

Crystalline forms of the HCl salt of Compound I other than Form C (Forms A, B and D) are also contemplated for the compositions and formulations of this disclosure. Such forms are described in WO 2016/179415, which is hereby incorporated by reference in its entirety.

Example 3: Capsule Formulations AA-AF

Several capsule formulations were made as shown in (Table 2). Initially, two 100 mg capsule formulations (Formulation AA and AB) were developed which differed only in the colour of the capsule shell. Subsequently, a preliminary 200 mg formulation (Formulation AC) was developed to provide higher dosage strengths. The initial formulations for both the 100 mg (Formulations AA and AB) and 200 mg (Formulation AC) were based on the same blend composition.

Two simpler 200 mg capsule formulations, Formulation AD, hard gelatine capsule shel,l and Formulation AE, hypromellose capsule shell, were then produced for clinical trial use. These formulations were based on the same primary blend composition (Compound I HCl and poloxamer 407) as in the 100 mg formulations (Formulations AA and AB) but included no additional excipients.

An optimized 200 mg capsule formulation (Formulation AF) was developed. No microcrystalline cellulose is included in the blend in contrast to the AA and AB Formulations. Formulation AF has a surprisingly better dissolution profile than Formulation AE. The development of this AF Formulation was also necessary in order to improve the manufacturability of the 200 mg strength capsule.

TABLE 2

Compound I Form C Capsule Formulations

| | | Formulation Number | | | | | | | |
|---|---|---|---|---|---|---|---|---|---|
| | | AA[a], AB | | AC | | AD[b], AE | | AF | |
| | | Dosage Strength | | | | | | | |
| | | 100 mg | | 200 mg | | 200 mg | | 200 mg | |
| | | Capsule | | | | | | | |
| | | Hard gelatine | | Hard gelatine | | AD. Hard gelatine AE. Hypromellose | | Hypromellose | |
| Component | Function | % w/w | mg/capsule | % w/w | mg/capsule | % w/w | mg/capsule | % w/w | mg/capsule |
| Compound I Form C | Active ingredient | 43.50 | 108.75 | 43.50 | 217.5 | 65.0 | 217.1 | 51.2 | 217.5 |
| Poloxamer 407 | Solubilizing Agent | 23.42 | 58.55 | 23.42 | 117.1 | 35.0 | 116.9 | 27.6 | 117.1 |
| Microcrystalline Cellulose | Excipient | 21.98 | 54.95 | 21.98 | 109.9 | — | — | — | — |
| Mannitol | Excipient | 7.60 | 19.0 | 7.60 | 38.0 | — | — | 16.8 | 71.3 |
| Crospovidone | Disintegrant | 3.00 | 7.5 | 3.00 | 15.0 | — | — | 3.0 | 12.8 |
| Magnesium Stearate | Lubricant | 0.50 | 1.25 | 0.50 | 2.5 | — | — | 1.5 | 6.4 |
| Total Fill Weight | | 100 | 250 mg | 100 | 500 mg | 100 | 334 mg | 100 | 425 mg |

[a] Formulations are identical except for colour of the capsule (Formulation AA uses a Swedish orange size 1 capsule and Formulation AB uses a blue opaque size 0 capsule.
[b] Formulations are identical except Formulation AD uses a hard gelatine capsule (opaque hard gelatine white size 0) and Formulation AE uses a Vcaps® Plus capsule (opaque hypromellose white size 0).

Example 4: Method for Making Formulations AA, AB and AC

1. Compound I Form C and poloxamer 407 were added to a blender and were blended.
2. The blended material was roller compacted blended to obtain a desired ribbon consistency. Screw speed, screw amps, roller speed, roller amps, roller pressure, and thickness [mm] were recorded.
3. Roller compacted ribbons were separated from fines using a screen. Fines were processed through a roller compaction process as needed.
4. The ribbons were passed through a mill equipped with an appropriate screen.
5. The milled material was charged to a blender and was blended.
6. The blended material was stored as necessary in an appropriately labelled (e.g., granulated material) double lined polyethylene bag container.
7. Formulations (AA) and (AB) 100 mg Capsules:
   a. The granulated material was added to a blender.
   b. Microcrystalline cellulose, mannitol, and crospovidone were each individually screened and charged into the blender.
   c. The remaining granulated material were charged to the blender and blended.
   d. Magnesium stearate was screened, charged to blender and blended.
8. Formulation (AC) 200 mg Capsules:
   a. Steps 7(a)-7(d) were followed, but twice the amount of starting materials were used for 200 mg capsules.
9. Samples were obtained for blend uniformity determination.
10. Capsule fill weight was determined based on mean blend uniformity results.
11. Capsules were filled using a dosator encapulator.
12. Capsules were dedusted and checked for metal contamination (this step can be conducted during or following encapsulation).
13. All acceptable capsules were processed through automatic weight sorter.

A list of representative equipment used in the manufacture of the Crystalline Form C of Compound I Capsules is provided in Table 3. Per scale-up and post-approval changes (SUPAC), any equivalent equipment of the same operating principle can be used. https://www.fda.gov/downloads/drugs/guidancecomplianceregulatoryinformation/guidances/ucm346049.pdf All other equipment is of standard pharmaceutical design (e.g., stainless steel vessels, size scales, etc).

TABLE 3

Representative Equipment List

| Unit Operation/ Operation Principle | Class/Subclass | Representative Equipment[a] |
|---|---|---|
| Blending and mixing/ Diffusion blending | Diffusion blender/ V-blender or bin blender | V-blender, bin blender |
| Dry Granulation | Dry granulator/ roller compaction | Vector Freund roller compactor (e.g., TF-156, WP 120) |
| Particle size reduction/ Screening | Cutting mill | Fitzmill |
| Unit dosing/Encapsulating | Encapsulator/ Dosator | Planeta MG2, Incap |

Process Controls—Formulations AA, AB and AC

Process controls are summarized in Table 4.

TABLE 4

| | | Process Controls | |
|---|---|---|---|
| Step | Test | Sample Interval | Acceptance Criteria/Descriptions |
| Step 9 | Blend uniformity | ~1 g from top, middle, bottom | 90-110% of label strength |

Example 5: Method for Making Formulation AD and AE

1. Compound I Form C and poloxamer 407 were added to a blender and blended.
2. The blended material was roller compacted, and was adjusted as necessary to obtain ribbon consistency. Screw speed, screw amps, roller speed, roller amps, roller pressure, and thickness (mm) were recorded.
3. The roller compacted ribbons were separated from fines using a screen. The fines were processed through a roller compaction process as needed.
4. The ribbons were passed through a mill equipped with an appropriate screen.
5. The milled material was charged to a blender and blended.
6. The blended material was stored as necessary in an appropriately labelled (e.g., granulated material) double-lined polyethylene bag container.
7. The granulated material was charged to a blender and blended.
8. Samples were obtained for blend uniformity determination.
9. Target capsule fill weight was determined based on mean blend uniformity results.
10. Capsules were filled using a dosator encapsulator.
11. Capsules were dedusted and checked for metal contamination (this step can be conducted during or following encapsulation).
12. All acceptable capsules were processed through an automatic weight sorter.

The equipment used in the manufacture of Formulation AD and AE are identical to that used for Formulation AF in Method 1 (Table 6). Per SUPAC, any equivalent equipment of the same operating principle can be used. All other equipment is of standard pharmaceutical design (e.g., stainless steel vessels, size scales, etc.).

Process Controls—Formulation AE

Process controls for the manufacture of Formulation AE are summarized in Table 5.

TABLE 5

| Process Controls—Formulation AE | |
|---|---|
| Test | Acceptance Criteria/Descriptions |
| Blend uniformity | 90-110% of label strength |
| Fill weight | 95-105% of target |

Example 6: Methods for Making Formulation AF

Method 1 for Making Formulation AF

Two manufacturing methods (Method 1 or Method 2) have been applied for formulation AF. These are different in mixing method of Compound I HCl and poloxamer 407 in the first mixing step. Details of these manufacturing methods are described as follows:

1. Mixing process: Compound I Form C and poloxamer 407 were mixed using a diffusion mixer.
2. Roller compaction process: The blended powders were compacted using a dry granulator (roller compactor) to provide ribbons.
3. Milling process: The roller compacted ribbons were passed through a cutting mill with an appropriate screen to provide appropriately-sized granules.
4. Blending process-I: The milled granules, mannitol and crospovidone were blended using a diffusion mixer.
5. Blending process-II: The blend obtained in blending process-I was blended with magnesium stearate using a diffusion mixer.
6. Encapsulation process: The final blend was filled into hypromellose capsules using an encapsulator.
7. Polishing process: The capsules were passed through a polisher.Weight check process: The capsules were passed through automatic weight sorter.
8. Packaging process: The capsules can optionally be packaged in high density polyethylene bottles with screw top polypropylene child-resistant caps and heat activated induction seal.

Method 2 for Making Formulation AF

1. Mixing process: Compound I Form C and poloxamer 407 were mixed using a convection mixer (vertical high intensity mixer).
2. Screening process: The mixture was screened using a screen (this process was conducted optionally).
3. Roller compaction process—The blended powders were compacted using a dry granulator (roller compactor) to provide ribbons.
4. Milling process: The roller compacted ribbons were passed through a screening mill with an appropriate screen and an impeller rotation speed to provide appropriately-sized granules.
5. Blending process-I: Milled granules, mannitol and crospovidone were blended using a diffusion mixer.
6. Blending process-II: The blend obtained in the blending process-I was blended with magnesium stearate using a diffusion mixer.
7. Encapsulation process: The final blend was filled using an encapsulator.
8. Polishing process: The capsules were passed through a polisher (this process was conducted optionally).
9. Weight check process: The capsules can be passed through automatic weight sorter.
10. Packaging process: The capsules can optionally be packaged in high density polyethylene bottles with screw top polypropylene child-resistant caps and heat activated induction seal.

A list of representative equipment used in the manufacture of Compound I Form C Capsules, Formulation AF, for Methods 1 and 2, is provided in Table 6. Any equivalent equipment of the same operating principle can be used. All other equipment is of standard pharmaceutical design (e.g., stainless steel vessels, size scales, etc.).

TABLE 6

Representative Equipment List—Formulation AF

| Step in Manufacture | Class/Subclass | |
|---|---|---|
| | Method 1 | Method 2 |
| Mixing | Diffusion Mixers (Tumble)/V-blender or bin blender | Convection mixers/Vertical high intensity mixers |
| Roller Compaction | Dry granulator/Roller compaction | Dry granulator/Roller compaction |
| Milling | Cutting mills | Screening mills/Rotating impeller |
| Blending | Diffusion Mixers (Tumble)/V-blender or bin blender | Diffusion Mixers (Tumble)/V-blender or bin blender |
| Encapsulation | Encapsulator/Dosator | Encapsulator/Dosator |

Process Controls—Formulation AF

The process controls for the manufacture of Compound I Form C Capsules, Formulation AF, are summarized in Tables 7 and 8.

The manufacturing process of AF capsules was optimized in Method 2. The differences between Method 2 and Method 1 are: (i) equipment class of the mixing process, (ii) the milling process, and (iii) addition of an optional screening process after the mixing process. These modifications reduce the lot-to-lot variation observed in the dissolution profile.

TABLE 7

Process Controls—Method 1

| Step | Test | Sample Interval | Acceptance Criteria/Descriptions |
|---|---|---|---|
| Step 4, Step 5 | Blend uniformity | ~0.425-1.275 g from top, middle, bottom | 90-110% of label strength |
| Step 6 | Mean capsule weight (N = 10) | Encapsulation start-up and during encapsulation | Mean capsule weight: mean target ± 5% |
| Step 7 | Capsule length | Encapsulation start-up and during encapsulation | Size 0 Go-No Go gauge |
| Step 8 | Individual weight | Weight sorting | Individual capsule weight: target ± 7% |

TABLE 8

Process Controls—Method 2

| Step | Test | Sample Interval | Acceptance Criteria/Descriptions |
|---|---|---|---|
| Step 7 | Mean capsule weight (N = 10) | Encapsulation start-up and during encapsulation | Mean capsule weight: mean target ± 5% |
| | Capsule length | Encapsulation start-up and during encapsulation | Size 0 Go-No Go gauge |
| Step 9 | Individual weight | Weight sorting | Individual capsule weight: Target ± 7% |

Dissolution Profile Examples for Formulations AA-AF

The dissolution tests were conducted under the conditions shown in Table 9.

The Dissolution Profiles of Formulations AA-AF below demonstrate that Formulation AF made by Method 1 has an unexpectedly better dissolution profile than the Formulations AA, AB, AC, AD, or AE, and that Formulation AF made by Method 2 has a better dissolution profile than Formulation AF made by Method 1.

Example 7: Dissolution Profile Comparison of Formulation AB (100 mg Dosage Strength) and Formulation AD (200 mg Dosage Strength)

Figure 5:
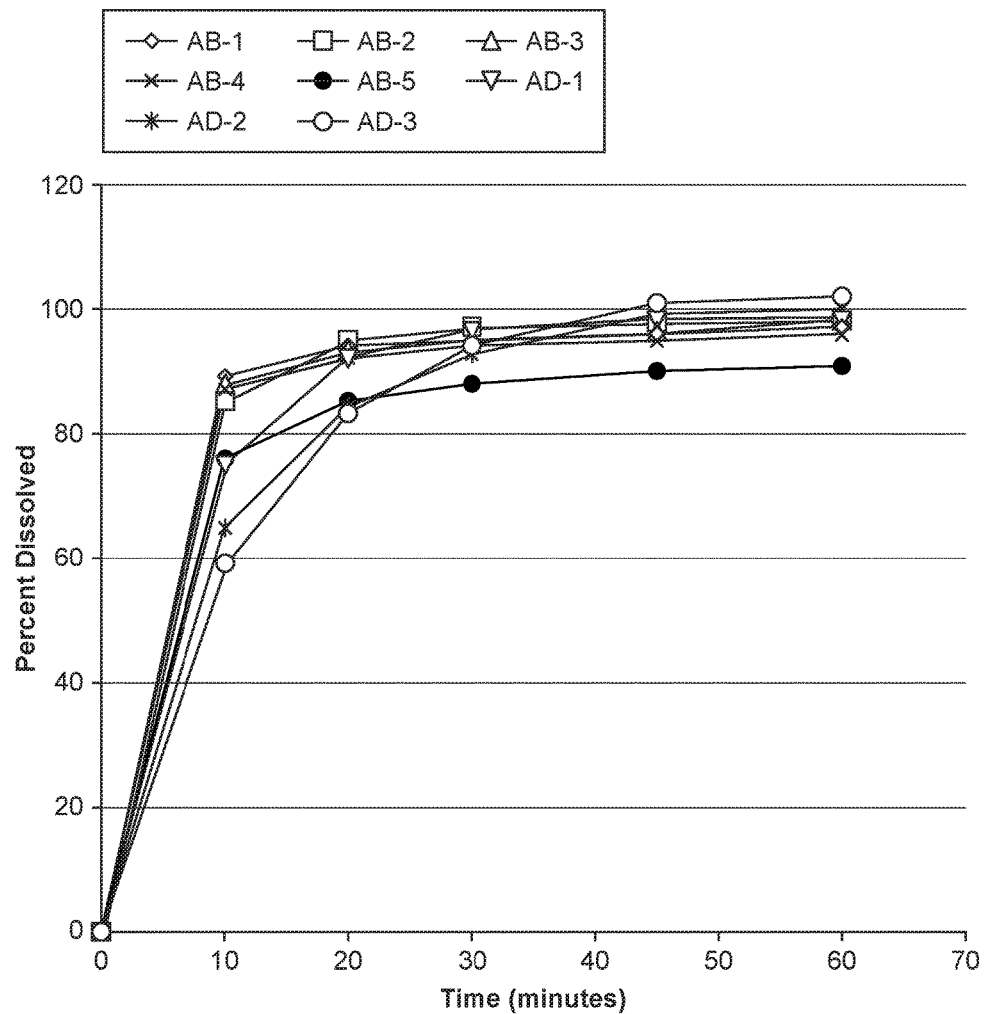
FIG. 5 is a comparison of in vitro dissolution profiles for five batches of AB Formulations (AB-1, "AB-2," "AB-3," "AB-4," and "AB-5") and three batches of AD Formulations ("AD-1," "AD-2," and "AD-3").

A comparison of in vitro dissolution profiles for five batches of AB Formulation (100 mg) and 3 batches of AD formulation (200 mg) demonstrated that these two formulations had comparable dissolution characteristics (>80% dissolved in 20 minutes). These dissolution profiles are shown in FIG. 5.

Example 8: Dissolution Profile Comparison of Formulations AD and AE

A dissolution evaluation comparing Compound I Form C in a hard gelatin capsule (Formulation AD) with Compound I Form C in an HPMC capsule (Formulation AE) was conducted. The compositions for formulations AD and AE were hand filled into the hard gelatin and HPMC capsules. The dissolution parameters are summarized in Table 9. For this dissolution evaluation, standard round bottom dissolution vessels were used. The results are summarized in Table 10. The results indicate that the dissolution profiles of hard gelatin and HPMC capsules are similar. The initial delay (at 10 and 20 minutes) in the HPMC profile is as expected and consistent with the profile shift reported by the HPMC capsule manufacturer, Capsugel.

TABLE 9

Dissolution Parameter Experimental Summary

| | |
|---|---|
| Apparatus | USP Apparatus 2 (paddles) with sinkers |
| Vessel | Round bottom vessel or PEAK vessel |
| Dissolution medium | 0.01N hydrochloric acid |
| Dissolution medium volume | 900 mL |
| Temperature | 37° C. |
| Speed | 75 rpm |

TABLE 10

Dissolution Comparison of Compound I Form C in Hard Gelatin (Formulation AD) and HPMC (Formulation AE) Capsules Using Round Bottom Dissolution Vessels

| | Percent Dissolved (N = 3) | |
|---|---|---|
| Time | Hard Gelatin Capsules (Formulation AD) | HPMC Capsules[a] (Formulation AE) |
| 10 minutes | | |
| Mean | 73.2 | 22.6 |
| Range | 63.9-78.9 | 22.4-23.0 |
| 20 minutes | | |
| Mean | 94.6 | 79.3 |
| Range | 91.9-96.6 | 66.9-87.6 |
| 30 minutes | | |
| Mean | 99.5 | 94.5 |
| Range | 97.3-101.0 | 87.1-99.2 |
| 45 minutes | | |
| Mean | 99.8 | 98.0 |
| Range | 97.5-101.3 | 97.0-99.7 |

TABLE 10-continued

Dissolution Comparison of Compound I Form C in Hard
Gelatin (Formulation AD) and HPMC (Formulation AE)
Capsules Using Round Bottom Dissolution Vessels

| | Percent Dissolved (N = 3) | |
|---|---|---|
| Time | Hard Gelatin Capsules (Formulation AD) | HPMC Capsules[a] (Formulation AE) |
| 60 minutes | | |
| Mean | 99.9 | 98.9 |
| Range | 97.5-101.4 | 98.0-100.0 |
| 90 minutes | | |
| Mean | 99.8 | 98.9 |
| zRange | 97.5-101.4 | 98.0-99.9 |

[a]Vcaps ® Plus capsules.

Figure 6:
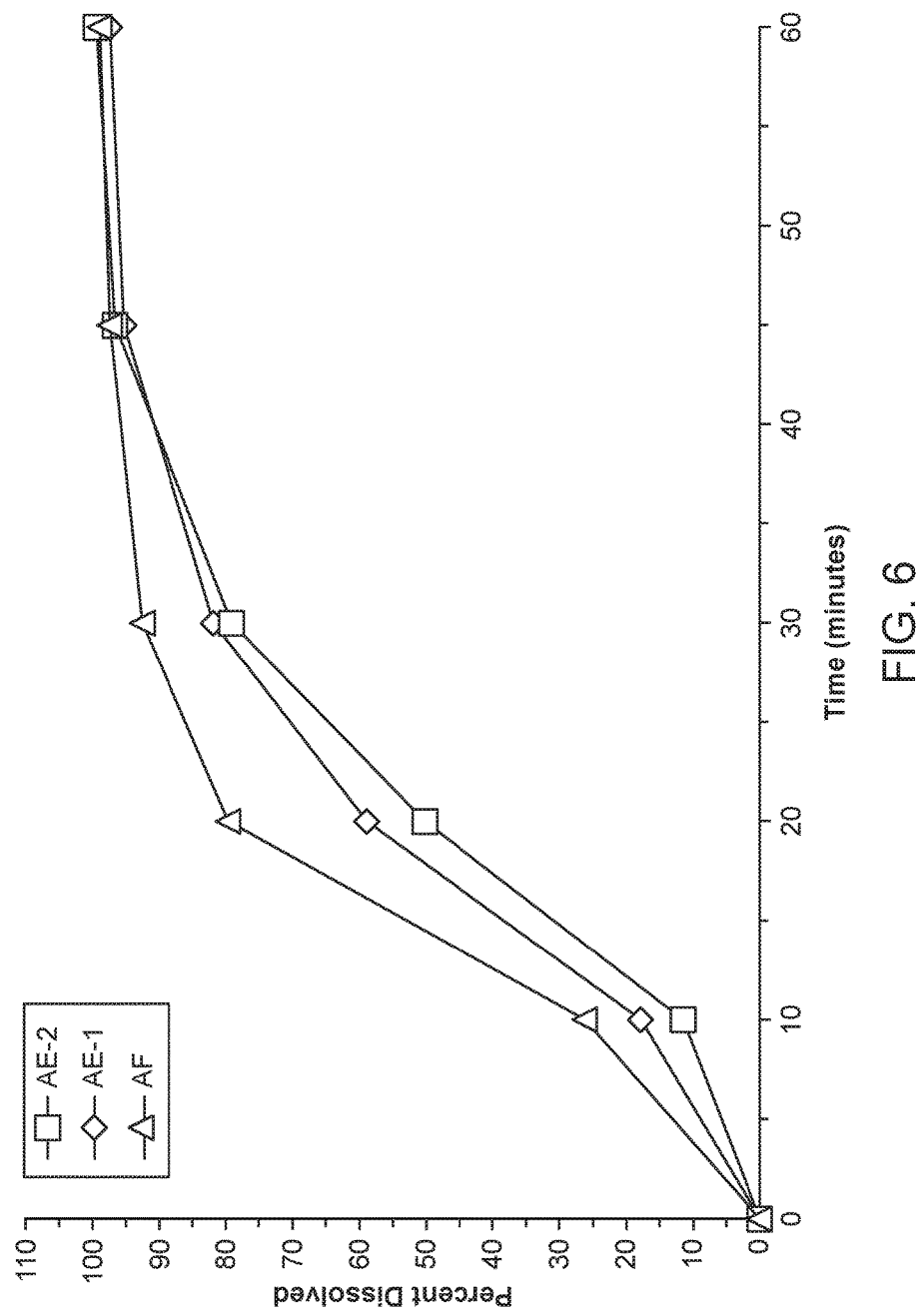
FIG. 6 is a dissolution comparison of two batches of 200 mg Formulation AE (diamond represents "AE-1", and square represents "AE-2") and Formulation AF (triangle represents "AF").

Example 9: Dissolution Profile of Formulation AF Made by Method 1 Compared to Dissolution Profiles of Formulations AA, AB, AC, AD and AE The dissolution profile of Formulation AF manufactured by Method 1 was compared to the dissolution profile of Formulation AE. A comparison of the in vitro dissolution profile of two batches of the AE formulation and one batch of the AF formulation is provided in Table 11 and FIG. 6. The $f_2$ values, using the 10-30 minute data, comparing the Formulation AF to Formulation AE, were 42 and 34, respectively. Accordingly, Formulation AF has a surprisingly better dissolution profile than Formulation AE.

TABLE 11

Comparison of 200 mg Formulation AE and Formulation AF

| Time (minutes) | Formulation AE) (N = 6) | Formulation AE) (N = 6) | Formulation AF (N = 6) |
|---|---|---|---|
| 0 | 0 | 0 | 0 |
| 10 | 17.8 | 11.5 | 26.2 |
| 20 | 58.9 | 50.2 | 79.6 |
| 30 | 81.8 | 79.1 | 92.5 |
| 45 | 95.3 | 96.6 | 97.4 |
| 60 | 97.4 | 99.4 | 98.9 |

Formulations AA, AB, AC and AD have about the same dissolution profile as Formulation AE for reasons stated herein, and which are reiterated below:
1. Formulation AE has about the same dissolution profile as AD (See Example 8 and Table 10).
2. Formulation AD has about the same dissolution profile as Formulation AB (See Example 7 and FIG. 5).
3. Formulations AB, AA and AC have the same composition that are in various hard gelatine capsules. The differences between these three formulations is not in the composition but (1) the color of the capsules between the AA Formulation (orange) and the AB Formulation (blue); and (2) the amount of composition in the Formulation AC (200 mg) and Formulations AA and AB (100 mg) (See Example 3 and Table 2).

Example 10: Dissolution Profile of Formulation AF Made by Method 1 Compared to Dissolution Profiles of Formulation AF Made by Method 2

Figure 7:
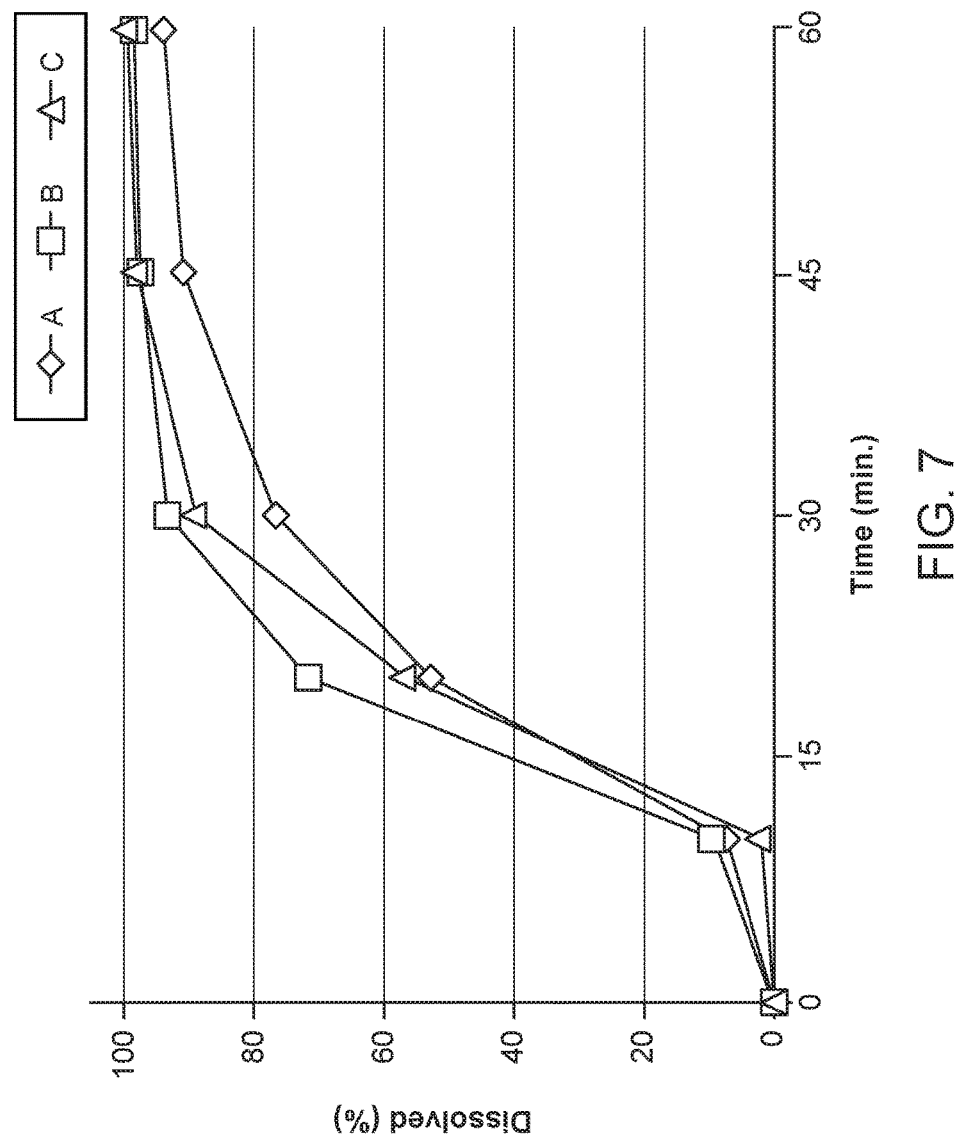
FIG. 7 shows dissolution profiles of the AF Formulations A, B, and C of Table 12 as manufactured by Method 1.

A lot-to-lot variation was observed in the dissolution profiles of Formulation AF manufactured by Method 1 as shown in Table 12 and FIG. 7.

TABLE 12

Dissolution profiles of three AF formulations (A, B, and C) manufactured by Method 1

| | A | B | C |
|---|---|---|---|
| | | Mixing Scale (g) | |
| | 430 | 70 | 70 |
| Time (min.) | | Percent Dissolved | |
| 0 | 0 | 0 | 0 |
| 10 | 7.7 | 9.9 | 2.3 |
| 20 | 52.9 | 72.0 | 57.4 |
| 30 | 76.5 | 93.6 | 89.3 |
| 45 | 90.6 | 97.7 | 98.3 |
| 60 | 93.9 | 98.4 | 99.6 |

Figure 8:
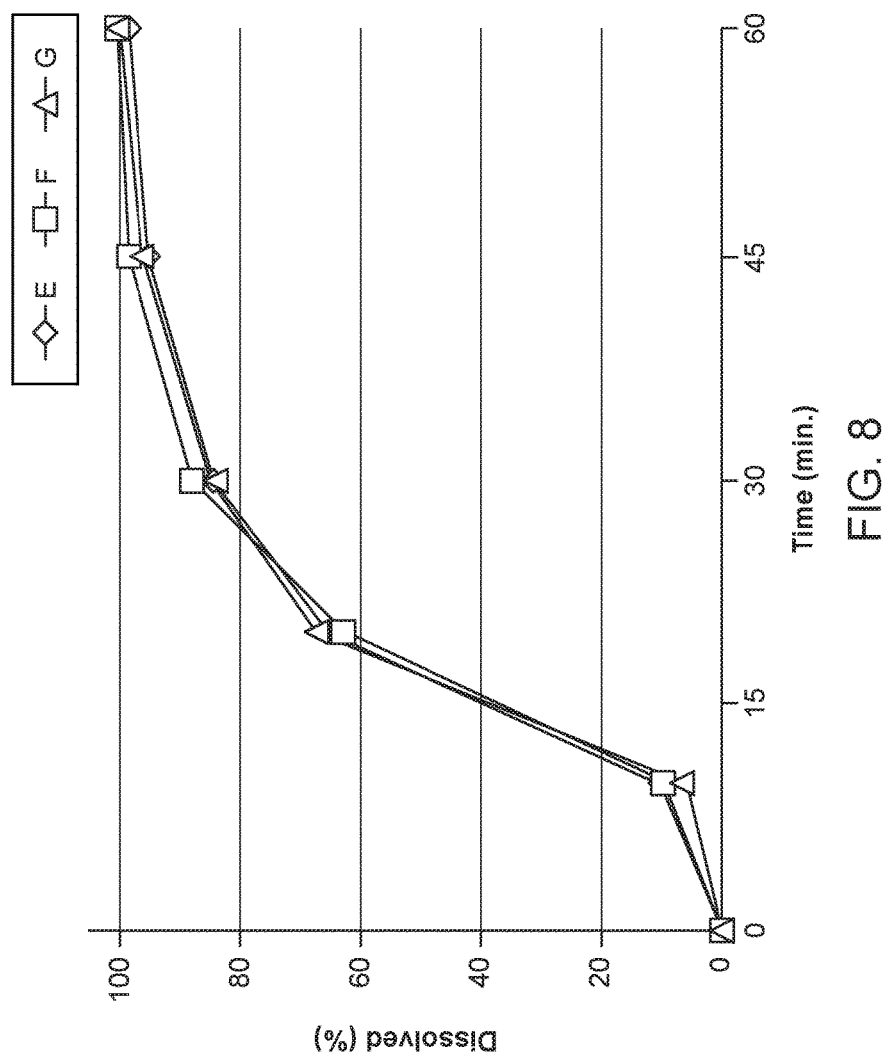
FIG. 8 shows dissolution profiles of the AF Formulations E, F, and G of Table 13 as manufactured by Method 2.

Formulation AF manufactured by Method 2 showed the constant dissolution profiles independent of mixing scale as shown in Table 13 and FIG. 8.

TABLE 13

Dissolution profiles of the AF formulations (E, F, and G) manufactured by Method 2

| | E | F | G |
|---|---|---|---|
| | | Mixing Scale (kg) | |
| | 42.5 | 10 | 0.4 |
| Time (min.) | | Percent Dissolved | |
| 0 | 0 | 0 | 0 |
| 10 | 10.3 | 10.3 | 7.1 |
| 20 | 65.0 | 62.9 | 66.4 |
| 30 | 85.0 | 87.9 | 84.7 |
| 45 | 95.3 | 98.2 | 96.4 |
| 60 | 98.8 | 100.3 | 100.1 |

These results demonstrated that the convection mixer is more appropriate equipment for mixing of Compound I HCl and poloxamer 407 than the diffusion mixer is.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

Thus, additional embodiments are within the scope of the disclosure and within the following claims.

What is claimed is:
1. A composition comprising: 40% to 60% W/W of Compound I having the following structure:

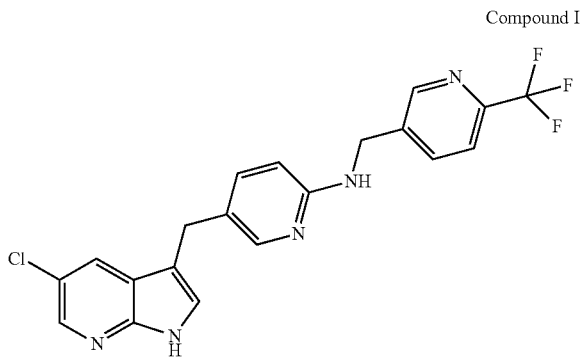 [SMILES: FC(F)(F)c1ccc(CNc2ccc(Cc3c[nH]c4ncc(Cl)cc34)cn2)cn1]

Compound I and wherein Compound I is a crystalline HCl salt characterized by an X-ray powder diffractogram comprising peaks (±0.2°) at 7.3, 23.3 and 28.2° 2θ as determined on a diffractometer using Cu-Kα radiation; 20% to 35% W/W of a poloxamer; 10% to 22% W/W of an excipient; 1% to 5% W/W of a disintegrant; and 0.5% to 3% W/W of a lubricant.

2. The composition of claim 1, wherein the poloxamer is poloxamer 407.

3. The composition of claim 1, wherein the diffractogram further comprises peaks at 16.6 and 20.9° 2θ±0.2°.

4. The composition of claim 1, wherein Compound I is characterized by:
  i) a diffractogram substantially as shown in FIG. 1;
  ii) a differential scanning calorimetry (DSC) thermogram comprising an endotherm at 234° C.;
  iii) a DSC thermogram substantially as shown in FIG. 2;
  iv) thermogravimetric analysis (TGA) comprising a thermogram substantially as shown in FIG. 3; or
  v) a dynamic vapor sorption (DVS) curve substantially as shown in FIG. 4.

5. The composition of claim 1, comprising 45% to 55% W/W of Compound I; 24% to 32% W/W of the poloxamer; 14% to 20% W/W of the excipient; 2% to 4% W/W of the disintegrant; and 1.0% to 2.5% W/W of the lubricant.

6. The composition of claim 1, comprising 48% to 53% W/W of Compound I; 26% to 29% W/W of the poloxamer; 15% to 18% W/W of the excipient; 2.5% to 3.5% W/W of the disintegrant; and 1.2% to 1.8% W/W of the lubricant.

7. The composition of claim 1, comprising 51.2% (±3%) W/W of Compound I; 27.6% (±3%) W/W of the poloxamer; 16.8% (±3%) W/W of the excipient; 3% (±1%) W/W of the disintegrant; and 1.5% (±1%) W/W of the lubricant.

8. The composition of claim 1, wherein the excipient is mannitol; the disintegrant is crospovidone; and the lubricant is magnesium stearate.

9. The composition of claim 8, wherein the crospovidone is Polyplasdone® Ultra or Polyplasdone® Ultra-10.

10. The composition of claim 1, wherein the poloxamer is poloxamer 407; the excipient is mannitol; the disintegrant is crospovidone; and the lubricant is magnesium stearate.

11. The composition of claim 10, comprising 45% to 55% W/W of Compound I; 24% to 32% W/W of poloxamer 407; 14% to 20% W/W of mannitol; 2% to 4% W/W of crospovidone; and 1.0% to 2.5% W/W of magnesium stearate.

12. The composition of claim 10, comprising 48% to 53% W/W of Compound I; 26% to 29% W/W of poloxamer 407; 15% to 18% W/W of mannitol; 2.5% to 3.5% W/W of crospovidone; and 1.2% to 1.8% W/W magnesium stearate.

13. The composition of claim 10, comprising 51.2% W/W (±3%) of Compound I; 27.6% W/W (±3%) of poloxamer 407; 16.8% (±3%) W/W of mannitol; 3% W/W (±1%) of crospovidone; and 1.5% (±1%) W/W of magnesium stearate.

14. The composition of claim 10, wherein the crospovidone is Polyplasdone® Ultra or Polyplasdone® Ultra-10.

15. The composition of claim 1, wherein the composition is in a capsule form suitable for oral dosage.

16. The composition of claim 15, wherein the capsule comprises hard gelatin or hypromellose.

17. The composition of claim 16, wherein the capsule comprises hypromellose.

18. A method for preparing the composition of claim 1 comprising mixing Compound I, and a poloxamer in a convection mixer.

19. The method of claim 18, wherein the convection mixer is a vertical high intensity mixer.

20. A composition prepared by the method of claim 18.

* * * * *